(12) United States Patent
Lee et al.

(10) Patent No.: US 12,158,774 B2
(45) Date of Patent: Dec. 3, 2024

(54) DISPLAY DEVICE

(71) Applicant: Samsung Display Co., Ltd., Yongin-Si (KR)

(72) Inventors: Seong Jun Lee, Seoul (KR); Won Ki Hong, Suwon-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 386 days.

(21) Appl. No.: 17/853,678

(22) Filed: Jun. 29, 2022

(65) Prior Publication Data

US 2023/0185333 A1   Jun. 15, 2023

(30) Foreign Application Priority Data

Dec. 9, 2021 (KR) .................. 10-2021-0175506

(51) Int. Cl.
    *G06F 1/16* (2006.01)
    *A61B 5/00* (2006.01)
    *A61B 5/021* (2006.01)
    *A61B 5/024* (2006.01)
    *G09G 3/00* (2006.01)

(52) U.S. Cl.
CPC ........ *G06F 1/1616* (2013.01); *A61B 5/02108* (2013.01); *A61B 5/02416* (2013.01); *A61B 5/6826* (2013.01); *A61B 5/6898* (2013.01); *A61B 5/742* (2013.01); *G06F 1/1684* (2013.01); *G09G 3/035* (2020.08); *A61B 2562/0247* (2013.01)

(58) Field of Classification Search
CPC ............ A61B 5/02108; A61B 5/02416; A61B 5/6826; A61B 5/6898; A61B 5/742
See application file for complete search history.

(56) References Cited

U.S. PATENT DOCUMENTS

| | | |
|---|---|---|
| 2017/0281024 A1 | 10/2017 | Narasimhan et al. |
| 2017/0360306 A1 | 12/2017 | Narasimhan et al. |
| 2019/0008399 A1 | 1/2019 | Mukkamala et al. |
| 2019/0104997 A1 | 4/2019 | Kang et al. |
| 2020/0085323 A1* | 3/2020 | Lee ............... A61B 5/02108 |

FOREIGN PATENT DOCUMENTS

| | | |
|---|---|---|
| KR | 10-2021-0028302 A | 3/2021 |
| KR | 10-2021-0033788 A | 3/2021 |

* cited by examiner

*Primary Examiner* — Abbas I Abdulselam
(74) *Attorney, Agent, or Firm* — Innovation Counsel LLP

(57) ABSTRACT

A display device includes a display panel, a first measurement enabling unit, a second measurement enabling unit, and a processor. The display panel may display an image. The display panel includes a first non-folding part, a second non-folding part, and a first folding part. The first non-folding part is connected through the folding part to the second non-folding part. The first measurement enabling unit is disposed in or overlaps with the first non-folding part and may emit first light. The second measurement enabling unit is disposed in or overlaps with the second non-folding part and may output a first signal in response to at least one of a received force and received light. The processor is connected to the second measurement enabling unit and may use the first signal to determine a blood pressure value.

20 Claims, 21 Drawing Sheets

DISPLAY DEVICE

CROSS-REFERENCE TO RELATED APPLICATION

This application claims priority to Korean Patent Application No. 10-2021-0175506 filed on Dec. 9, 2021 in the Korean Intellectual Property Office; the Korean Patent Application is incorporated by reference.

BACKGROUND

1. Technical Field

The technical field is related to a display device.

2. Description of the Related Art

A display device may display an image in response to input signals. Display devices are included in various electronic devices, such as televisions, monitors, smartphones, and tablet personal computers. Additional functional units, such as a camera and/or a fingerprint sensor, may be included in a display device. Electronic devices and/or display devices may be used for obtaining biometric information related to health.

SUMMARY

Aspects of the present disclosure provide a display device capable of accurately measuring a user's blood pressure by analyzing a photoplethysmographic signal.

Aspects of the present disclosure also provide a display device capable of more easily measuring a user's blood pressure using a folding structure of the display device and a pulse wave signal detection structure in a folded state thereof.

However, aspects of the present disclosure are not restricted to those set forth herein. The above and other aspects of the present disclosure will become more apparent to one of ordinary skill in the art to which the present disclosure pertains by referencing the detailed description of the present disclosure given below.

According to an embodiment of the disclosure, a display device comprising a display panel configured to display an image in a plurality of non-folding areas and at least one folding area, a first pulse wave signal detection region disposed in a first non-folding area among the plurality of non-folding areas to emit light, a second pulse wave signal detection region disposed in a second non-folding area among the plurality of non-folding areas to sense a force applied from an outside and light received on a front side, and a main processor configured to generate a pulse wave signal according to an optical signal generated in the second pulse wave signal detection region, and measure a user's blood pressure using an analysis result of a magnitude, a period, and a wave change of the pulse wave signal.

In an embodiment, the first and second non-folding areas of the display panel are disposed in a first direction with a first folding area interposed therebetween, and the second non-folding area and a third non-folding area are disposed in the first direction with a second folding area interposed therebetween.

In an embodiment, the first folding area is folded in an in-folding or out-folding manner in the first direction, and the second folding area is folded in an in-folding or out-folding manner in the first direction differently from the first folding area.

In an embodiment, a width of the first folding area in the first direction is formed to be different from a width of the second folding area in the first direction, the first folding area is folded in an in-folding or out-folding manner in the first direction, and the second folding area is folded in an in-folding or out-folding manner in the first direction in the same way as the first folding area.

In an embodiment, the first pulse wave signal detection region comprises a plurality of image display pixels and a light emitting member disposed in at least one through hole, and emits light to the front side using the plurality of image display pixels or the light emitting member.

In an embodiment, the second pulse wave signal detection region comprises a force sensor formed in the display panel to detect the force applied from the outside, a temperature sensor disposed on one surface of the display panel to sense a temperature of the display panel, a plurality of image display pixels formed on the display panel, and a plurality of light sensing pixels comprising a light receiving sensor and formed on the display panel.

In an embodiment, the force sensor is formed on a touch sensing layer of the display panel or is disposed on a rear surface of the display panel, and the temperature sensor is formed on the front surface or the rear surface of the display panel.

In an embodiment, the plurality of light sensing pixels comprising the light receiving sensor are disposed between the plurality of image display pixels to detect an amount of light incident from the front side, and transmit an optical signal according to the detected amount of light to the main processor.

In an embodiment, the main processor generates temperature data according to a temperature sensing signal inputted from the temperature sensor, compares the temperature data with a preset temperature reference value, and corrects a force data size of the force sensor to a size corresponding to a difference value obtained by the comparison.

In an embodiment, the main processor generates the pulse wave signal according to an amount of light sensed by the light receiving sensor and the optical signal corresponding to the amount of light, calculates a peak detection value of the pulse wave signal and detection time information of the peak detection value, and calculates information on a diastolic blood pressure, a mean blood pressure, and a systolic blood pressure by analyzing pulse wave signal values during previous and subsequent periods predetermined based on a detection time of the peak detection value.

In an embodiment, the main processor sets, as the diastolic blood pressure, a blood pressure value according to a pulse wave signal detection value at any one time in a range of 60 percent to 80 percent of the predetermined previous period before the detection time of the peak detection value, sets, as the systolic blood pressure, a blood pressure value according to a pulse wave signal detection value at any one time in a range of 40 percent to 60 percent of the predetermined subsequent period after the detection time of the peak detection value, and sets the mean blood pressure with respect to the diastolic blood pressure to the systolic blood pressure.

In an embodiment, the main processor sets, as the diastolic blood pressure, a blood pressure value according to a pulse wave signal detection value of 70 percent compared to the peak detection value in the predetermined previous period before the detection time of the peak detection value, sets, as the systolic blood pressure, a blood pressure value according to a pulse wave signal detection value of 50 percent compared to the peak detection value in the predetermined subsequent period after the detection time of the peak detection value, and sets the mean blood pressure with respect to the diastolic blood pressure to the systolic blood pressure.

In an embodiment, if the peak detection value of the pulse wave signal is not set, the main processor calculates an average pulse wave signal value and a lowest pulse wave signal value during a detection period of the peak detection value, sets, the mean blood pressure, a blood pressure value corresponding to the average pulse wave signal value, and sets or resets the systolic blood pressure and the diastolic blood pressure using Equation 1 below, $$SBP = \alpha \times MBP - \beta \times DBP$$

$$DBP = (\alpha \times MBP - SBP)/\beta \qquad \text{[Equation 1]}$$

where $\alpha$ and $\beta$ are natural numbers except zero, which are equal to or different from each other, the SBP is a systolic blood pressure, the DBP is a diastolic blood pressure, and the MBP is a mean blood pressure.

In an embodiment, a front surface of the first non-folding area is disposed to face a front surface of the second non-folding area by in-folding of the at least one folding area, and the first pulse wave signal detection region is disposed to face the second pulse wave signal detection region by disposition of the first and second non-folding areas facing each other.

According to an embodiment of the disclosure, a display device comprising a display panel configured to display an image in a plurality of non-folding areas and at least one folding area, a pulse wave signal detection region disposed in any one of the plurality of non-folding areas to sense a force applied from an outside and light received on a front side; and a main processor configured to generate a pulse wave signal according to an optical signal generated in the pulse wave signal detection region, and measure a user's blood pressure using an analysis result of a magnitude, a period, and a wave change of the pulse wave signal.

In an embodiment, the pulse wave signal detection region comprises a force sensor formed on the display panel to detect the force applied from the outside, a temperature sensor disposed on one surface of the display panel to sense a temperature of the display panel, a plurality of image display pixels formed on the display panel, and a plurality of light sensing pixels comprising a light receiving sensor and formed on the display panel.

In an embodiment, the pulse wave signal detection region comprises a force sensor disposed on one surface of the display panel to sense the force applied from the outside, a light receiving sensor disposed in a through hole toward the front side of the display panel to sense light incident from the front side of the display panel, and a temperature sensor disposed on one surface of the display panel to sense a temperature of the display panel.

In an embodiment, the main processor generates temperature data according to a temperature sensing signal inputted from the temperature sensor, compares the temperature data with a preset temperature reference value, and corrects a force data size of the force sensor to a size corresponding to a difference value obtained by the comparison.

In an embodiment, the pulse wave signal detection region is disposed to overlap the through hole of the display panel in a thickness direction of the display panel, and further comprises a light emitting member emitting light, and the light receiving sensor is configured to sense light reflected by an object or a body part on the other surface opposite to one surface of the display panel among lights emitted from the light emitting member through the through hole.

In an embodiment, the main processor generates the pulse wave signal according to an amount of light sensed by the light receiving sensor and the optical signal corresponding to the amount of light, calculates a peak detection value of the pulse wave signal and detection time information of the peak detection value, and calculates information on a diastolic blood pressure, a mean blood pressure, and a systolic blood pressure by analyzing pulse wave signal values during previous and subsequent periods predetermined based on a detection time of the peak detection value.

An embodiment may be related to a display device. The display device may include a display panel, a first measurement enabling unit, a second measurement enabling unit, and a processor. The display panel may display an image. The display panel may include a first non-folding part, a second non-folding part, and a first folding part. The first non-folding part may be connected through the folding part to the second non-folding part. The first measurement enabling unit may be disposed in or overlap with the first non-folding part and may emit first light. The second measurement enabling unit may be disposed in or overlap with the second non-folding part and may output a first signal in response to at least one of a received force and received light. The processor may be (electrically and/or optically) connected to the second measurement enabling unit and may use the first signal to determine a blood pressure value.

The display panel may include a second folding part and a third non-folding part. The first folding part may be positioned between the first non-folding part and the second non-folding part in a first direction when the display panel is unfolded. The second folding part may be positioned between the first non-folding part and the third non-folding part in the first direction when the display panel is unfolded.

When the first folding part may be folded in an in-folding manner, the first measurement enabling unit may overlap the second measurement enabling unit.

A width of the first folding part in the first direction may be different from a width of the second folding part in the first direction when the display panel is completely unfolded.

The first measurement enabling unit may include at least one of a first light emitting pixel set and a first light emitting member configured to emit the first light. The first non-folding part may include at least one of a first hole and a first transparent part configured to transmit the first light.

The second measurement enabling unit may include the following elements: a force sensor configured to detect the received force; a temperature sensor configured to sense a temperature of the display panel; a second light emitting pixel set; and a light sensor set. At least one of the force sensor and the temperature sensor may overlap at least one of a light emitting pixel of the second light emitting pixel set and a light sensor of the light sensor set.

The force sensor may include at least one of an opening and a transparent member that overlap with both the second light emitting pixel set and the light sensor set.

Light sensors of the light sensor set and light emitting pixels of the second light emitting pixel set may be alternately disposed. The light sensor set may generate the first signal according to an amount of the received light.

The processor may generate temperature data according to a temperature sensing signal inputted from the temperature sensor, may compare the temperature data with a preset temperature reference value to generate a difference value, and may correct a force data size of the force sensor to a size corresponding to the difference value.

The processor may generate a wave signal according to the first signal, may identify a peak value of the wave signal, may identify a peak value time corresponding to the peak value, and may determine values of a diastolic blood pressure, a mean blood pressure, and a systolic blood pressure by analyzing values in the wave signal during a preceding period and a subsequent period. The preceding period precedes the peak value time. The subsequent period follows the peak value time.

The processor may set a blood pressure value according to a wave signal value at a time in a range of 60 percent to 80 percent of the preceding period as a value of the diastolic blood pressure. The processor may set a blood pressure value according to a wave signal value at a time in a range of 40 percent to 60 percent of the subsequent period as a value of the systolic blood pressure. The processor may calculate the mean blood pressure using the diastolic blood pressure and the systolic blood pressure.

The processor may set a blood pressure value according to a wave signal value of 70 percent of the preceding period as the value of the diastolic blood pressure. The processor may set a blood pressure value according to a wave signal value of 55 percent of the subsequent period as the value of the systolic blood pressure.

If the peak value of the wave signal is not determined during a detection period of the peak value, the processor may calculate an average wave signal value and a lowest wave signal value, may set a value of the mean blood pressure according to an average wave signal value, and may set or reset values of the systolic blood pressure and the diastolic blood pressure using Equations 1:

$$SBP = \alpha \times MBP - \beta \times DBP$$

$$DBP = (\alpha \times MBP - SBP)/\beta \qquad [\text{Equations 1}]$$

The $\alpha$ and the $\beta$ may be positive integers that may be equal to or different from each other. The SBP may be a value of the systolic blood pressure, the DBP may be a value of the diastolic blood pressure, and the MBP may be the value of the mean blood pressure.

The first measurement enabling unit may overlap the second measurement enabling unit when an image display surface of the first non-folding part faces an image display surface of the second non-folding part.

An embodiment may be related to a display device. The display device may include a display panel, a measurement enabling unit, and a processor. The display panel may display an image. The display panel may include a first non-folding part, a second non-folding part, and a first folding part. The first non-folding part may be connected through the folding part to the second non-folding pan. The measurement enabling unit may be disposed in or overlap with the first non-folding part and may output a first signal in response to at least one of a received force and received light. The processor may be (electrically and/or optically) connected to the measurement enabling unit and may use the first signal to determine a value of a user's blood pressure.

The measurement enabling unit may include the following elements: a force sensor formed configured to detect the received force; a temperature sensor configured to sense a temperature of the display panel; at least one light emitting element spaced from at least one of the force sensor and the temperature sensor; and at least one light sensor spaced from one or both of the force sensor and the temperature sensor.

The measurement enabling unit may include the following elements: a force sensor configured to sense the received force and may include at least one of an opening and a transparent part; a light sensor overlapped with the at least one of the opening and the transparent part and configured to sense the received light; and a temperature sensor spaced from the light sensor and configured to sense a temperature of the display panel.

The processor may generate temperature data according to a temperature sensing signal inputted from the temperature sensor, may compare the temperature data with a preset temperature reference value to generate a difference value, and may correct a force data size of the force sensor according to the difference value.

The display panel may include at least one of a hole and a transparent member. The measurement enabling unit may overlap with at the at least one of the hole and the transparent member in a thickness direction of the display panel. The measurement enabling unit may include a light emitting member configured to emit emitted light. The received light may be a reflected portion of the emitted light.

The processor may generate a wave signal according to the first signal, may identify a peak value of the wave signal, may identify a peak value time corresponding to the peak value, and may determine values of a diastolic blood pressure, a mean blood pressure, and a systolic blood pressure by analyzing values in the wave signal during a preceding period and a subsequent period. The preceding period precedes the peak value time. The subsequent period follows the peak value time.

According to embodiments, light that has reached a user's body part or has been reflected from a user's body part after being emitted from a display panel is sensed by a light receiving sensor implemented on or in a display panel. The user's blood pressure may be measured by analyzing a pulse wave signal according to the amount of the sensed light.

According to embodiments, a user's blood pressure may be easily measured using a display device.

DETAILED DESCRIPTION

Figure 1:
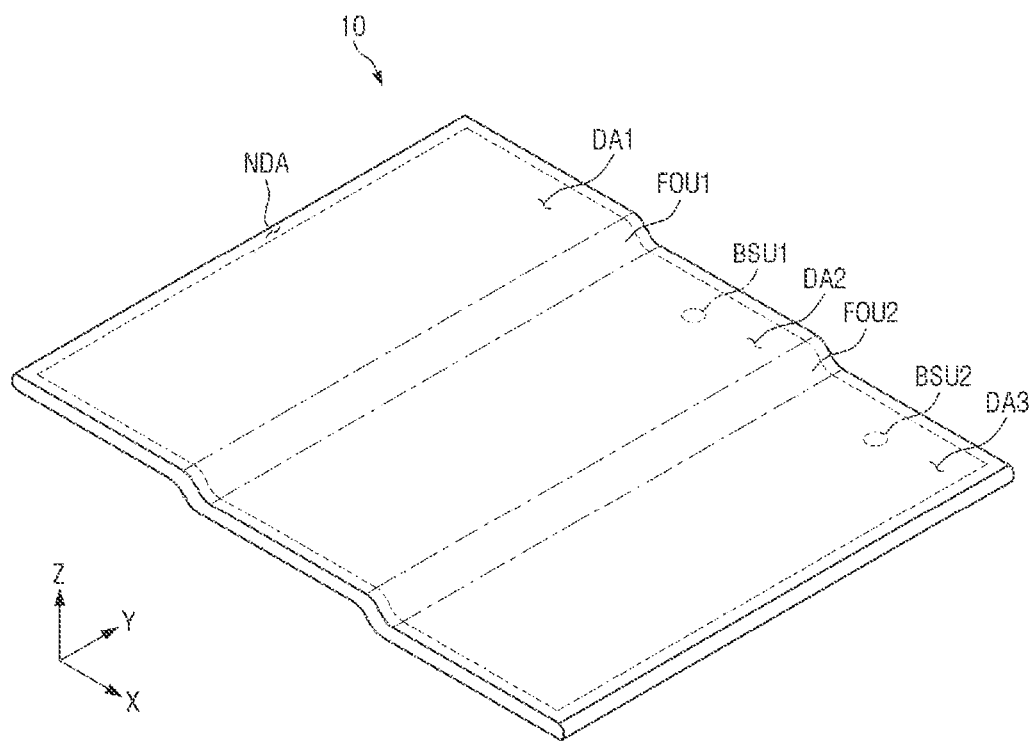
FIG. 1 is a schematic perspective view showing a display device according to one embodiment.

Examples of embodiments are described with reference to the accompanying drawings. Practical embodiments may be embodied in different forms and should not be construed as limited to the described embodiments.

The same reference numbers may indicate the same components or analogous components.

Although the terms "first," "second," etc. may be used to describe various elements, these elements should not be limited by these terms. These terms may be used to distinguish one element from another element. A first element may be termed a second element without departing from the teachings of one or more embodiments. A second element may be termed a first element. The description of an element as a "first" element may not require or imply the presence of a second element or other elements. The terms "first," "second," etc. may be used to differentiate different categories or sets of elements. For conciseness, the terms "first," "second," etc. may represent "first-category (or first-set)," "second-category (or second-set)," etc., respectively.

Features of the various embodiments may be combined with each other, in part or in whole. Embodiments may be implemented independently of each other or may be implemented together in an association.

The term "on" may mean "directly on" or "indirectly on." The term "connect" may mean "directly connect" or "indirectly connect." The term "connect" may mean "mechanically connect" and/or "electrically connect." The term "connected" may mean "electrically connected" or "electrically connected through no intervening transistor." The term "insulate" may mean "electrically insulate" or "electrically isolate." The term "conductive" may mean "electrically conductive." The term "drive" may mean "operate" or "control." The term "include" may mean "be made of." The term "adjacent" may mean "immediately adjacent." The expression that an element extends in a particular direction may mean that the element extends lengthwise in the particular direction and/or that the lengthwise direction of the element is in the particular direction. The term "pattern" may mean "member." The term "define" may mean "form" or "provide." The expression that a space or opening overlaps an object may mean that (the position of) the space or opening overlaps with (the position of) the object. The term "overlap" may be equivalent to "be overlapped by." The expression that a first element overlaps with a second element in a plan view may mean that the first element overlaps the second element in direction perpendicular to a substrate. The term "front surface" may mean "display surface." The term "rear surface" may mean "non-display surface." The term "above" may mean "in front of." The term "under" or "below" may mean "behind." The term "top" may mean "front." The term "bottom" may mean "back." The term "area" may mean "part." The term "region" may mean "part" or "unit." The term "pulse wave signal detection region" may mean "blood pressure measurement enabling unit" or "measurement enabling unit." The term "previous" may mean "preceding."

Figure 2:
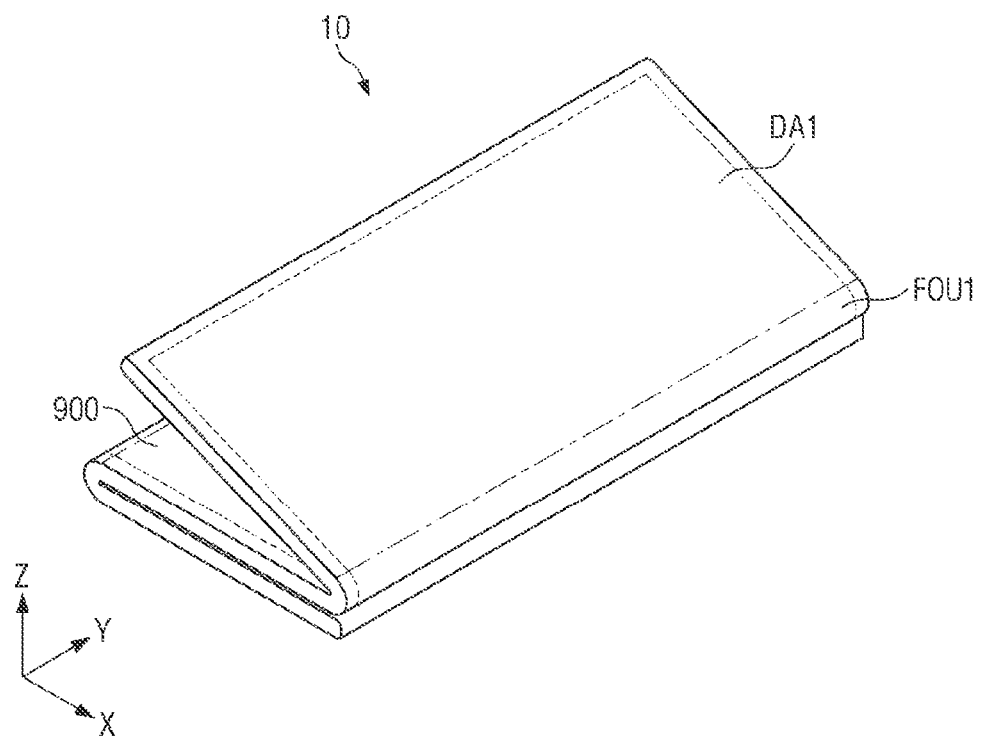
FIG. 2 is a perspective view illustrating a multi-folding shape/form of a display device according to one embodiment.
Figure 3:
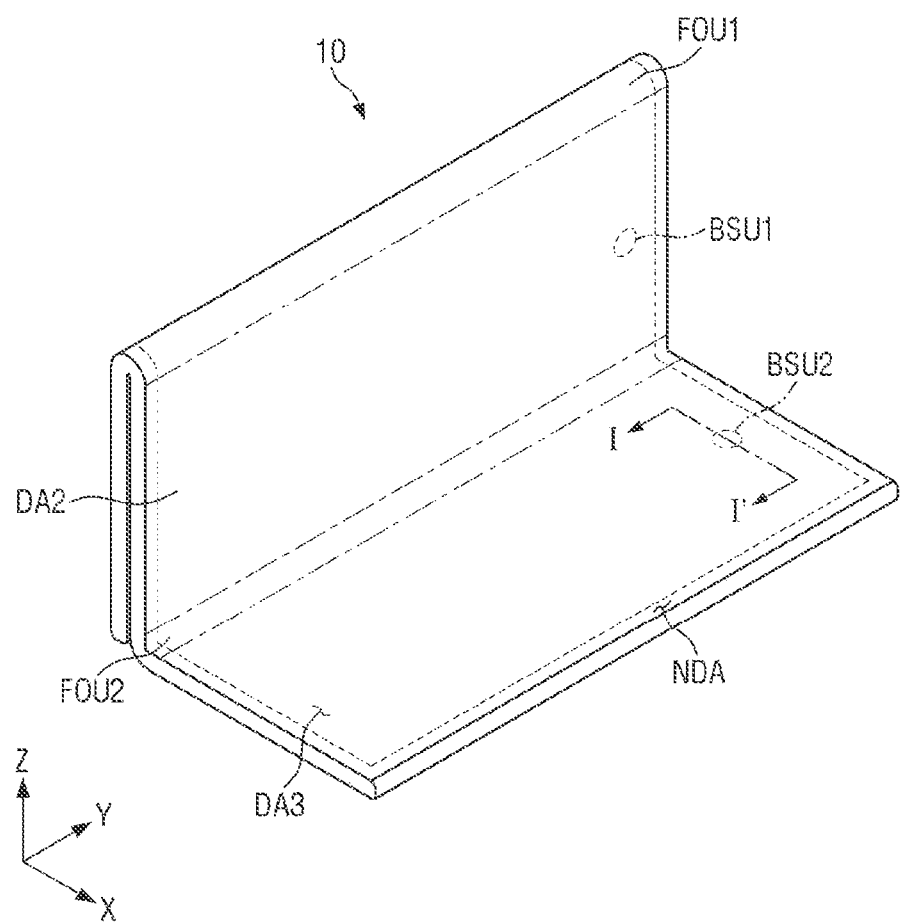
FIG. 3 is a perspective view illustrating a multi-folding shape of a display device according to one embodiment.

FIG. 1 is a schematic perspective view showing a display device 10 according to one embodiment. FIG. 2 is a perspective view illustrating a multi-folding shape/form of the display device 10 according to one embodiment. FIG. 3 is a perspective view illustrating another multi-folding shape of the display device 10 according to one embodiment.

Referring to FIGS. 1 to 3, the display device 10 may include multi-folding structures. The display device may be included in a mobile phone, a smartphone, a tablet personal computer, a mobile communication terminal, an electronic organizer, an electronic book, a portable multimedia player (PMP), a navigation system, an ultra-mobile PC (UMPC), a television, a laptop computer, a monitor, a billboard, or an Internet-of-Things (IoT) terminal.

In the description, a first direction (X-axis direction) may be a short side direction of the display device 10 in a folded state and may be a horizontal/width direction of the display device 10. A second direction (Y-axis direction) may be a long side direction of the display device 10 in a folded state and may be a vertical/height/length direction of the display device 10. A third direction (Z-axis direction) may be a thickness/depth direction of the display device 10. The multi-folding structures enable the display device to be folded at multiple lines.

FIGS. 1 to 3 illustrate the display device 10 as a multi-foldable display device that is foldable at multiple lines that extend in the second direction (Y-axis direction). The display device 10 may maintain a folded state, in which it is folded at one or more lines, or may maintain a completely unfolded state. The display device 10 may be folded in an in-folding manner in which the front surface as an image display surface is substantially concealed. When the display device 10 is bent or folded in the in-folding manner, display surfaces of the display device 10 may face each other. The display device 10 may be folded in an out-folding manner in which an image display surface is exposed. If the display device 10 is bent or folded in an out-folding manner, the non-display surfaces of the display device 10 may face each other.

The entire image display area of the display device 10 may be include non-folding areas DA1 to DA3 and may include one or more folding areas FOU1 and FOU2. The first and second folding areas FOU1 and FOU2 may be disposed at different locations in the first direction (X-axis direction) and may extend in the second direction (Y-axis direction). The first folding area FOU1 may be disposed between the first and second non-folding areas DA1 and DA2 in the first direction (X-axis direction). The second folding area FOU2 may be disposed between the second and third non-folding areas DA2 and DA3 in the first direction (X-axis direction). An image non-display area NDA may be formed at the outer periphery of the entire image display area, that is, outside the non-folding areas DA1 to DA3 and the folding areas FOU1 and FOU2.

The first folding area FOU1 may extend in the second direction (Y-axis direction) between the first and second non-folding areas DA1 and DA2. The first folding area FOU1 may be folded in the in-folding or out-folding manner in the first direction (X-axis direction). When the first folding area FOU1 is folded in the out-folding manner, the rear/non-display surfaces opposite the first and second non-folding areas DA1 and DA2 may face each other. When the first folding area FOU1 is folded in the in-folding manner, the front/display surfaces of the first and second non-folding areas DA1 and DA2 may face each other. When the first folding area FOU1 extends in the second direction (Y-axis direction) and is in-folded or out-folded in the first direction (X-axis direction), the width of the display device 10 in the first direction (X-axis direction) may be reduced to approximately ⅔ of its initial/un-folded value.

The second folding area FOU2 may extend in the second direction (Y-axis direction) between the second and third non-folding areas DA2 and DA3. The second folding area FOU2 may be folded in the in-folding or out-folding manner in the first direction (X-axis direction). When the second folding area FOU2 is folded in the in-folding manner, the front/display surfaces of the second and third non-folding areas DA2 and DA3 may face each other. When the second folding area FOU2 is folded in the out-folding manner, the rear/non-display surfaces of the second and third non-folding areas DA2 and DA3 may face each other. When the second folding area FOU2 extends in the second direction (Y-axis direction) and is in-folded or out-folded in the first direction (X-axis direction), the width of the display device 10 in the first direction (X-axis direction) may be reduced to approximately ⅔ of its initial/unfolded value.

As illustrated in FIGS. 2 and 3, the multi-foldable type display device 10 may have an S type or inverted S type foldable structure in which the first folding area FOU1 is folded in the out-folding manner so that the rear surfaces of the first and second non-folding areas DA1 and DA2 face each other, and the second folding area FOU2 is folded in the in-folding manner so that the front surfaces of the second and third non-folding areas DA2 and DA3 face each other. In the S type or inverted S type structure, when the first and second folding areas FOU1 and FOU2 are in-folded or out-folded, the width of the display device 10 in the first direction (X-axis direction) may be reduced to approximately ⅓ of its initial/unfolded value. Therefore, a user can conveniently carry the display device 10.

One or more folding areas may be disposed at different locations in the second direction (Y-axis direction) and extend in the first direction (X-axis direction). In this case, the folding areas may be folded in the second direction (Y-axis direction), and non-folding areas may be folded in the second direction (Y-axis direction).

When the first and second folding areas FOU1 and FOU2 are disposed in the first direction (X-axis direction) and extend in the second direction (Y-axis direction), the width of each of the first and second folding areas FOU1 and FOU2 in the first direction (X-axis direction) is smaller than the length thereof in the second direction (Y-axis direction). The width of the first non-folding area DA1 in the first direction (X-axis direction) may be greater than the width of the first folding area FOU1 in the first direction (X-axis direction). The width of the second non-folding area DA2 in the first direction (X-axis direction) may also be greater than the width of the first folding area FOU1 in the first direction (X-axis direction). The width of the third non-folding area DA3 in the first direction (X-axis direction) may be greater than the width of the second folding area FOU2 in the first direction (X-axis direction). For smoothly folding the first and second folding areas FOU1 and FOU2 and arranging the first to third non-folding areas DA1 to DA3, the widths of the first and second folding areas FOU1 and FOU2 in the first direction (X-axis direction) may be different from each other.

The entire image display surface, i.e., the image display area of the display device 10 may be disposed on the front side of the display device 10 in the third direction (Z-axis direction). The image display area of the display device 10 may include the first non-folding area DA1, the first folding area FOU1, the second non-folding area DA2, the second folding area FOU2, and the third non-folding area DA3. When the display device 10 is unfolded as shown in FIG. 1, an image may be displayed toward the front side in the first non-folding area DA1, the first folding area FOU1, the second non-folding area DA2, the second folding area FOU2, and the third non-folding area DA3 of the display device 10.

As shown in FIGS. 2 and 3, the second folding area FOU2 is in-folded so that the second and third non-folding areas DA2 and DA3 face each other, and the first folding area FOU1 is out-folded so that the first non-folding area DA1 may be exposed. In this case, an image may be displayed toward the front side only in the first non-folding area DA1.

In at least one non-folding area of the first to third non-folding areas DA1 to DA3, one or more pulse wave signal detection regions/units (or measurement enabling units) BSU1 and BSU2 may be configured to apply light to a user's specific body part such as a finger, and may sense light that has passed through the body part or has been reflected from the body part. In at least one of the pulse wave signal detection regions BSU1 and BSU2, a pulse wave signal according to the amount of sensed light may be detected and transmitted to the main processor 710 illustrated in FIG. 4. One or more pulse wave signal detection regions BSU1 and BSU2 may be formed in one or more of the first to third non-folding areas DA1 to DA3 (e.g., the second and third non-folding areas DA2 and DA3).

FIGS. 1 and 3 illustrate that the first and second pulse wave signal detection regions BSU1 and BSU2 are respectively formed the second and third non-folding areas DA2 and DA3 among the first to third non-folding areas DA1 to DA3. One pulse wave signal detection region of the first and second pulse wave signal detection regions BSU1 and BSU2 may allow image display light for displaying an image and/or light emitted from a light emitting member to be applied to a user body part. In the other pulse wave signal detection region of the first and second pulse wave signal detection regions BSU1 and BSU2, light that has passed through the user body part and/or light that has reflected from the user body part may be sensed by a light receiving sensor. The pulse wave signal according to the amount of sensed light may be detected and transmitted to at least the main processor 710. The main processor 710 may analyze the pulse wave signal according to the amount of light sensed through the first and second pulse wave signal detection regions BSU1 and BSU2 to determine a user's blood pressure.

Figure 4:
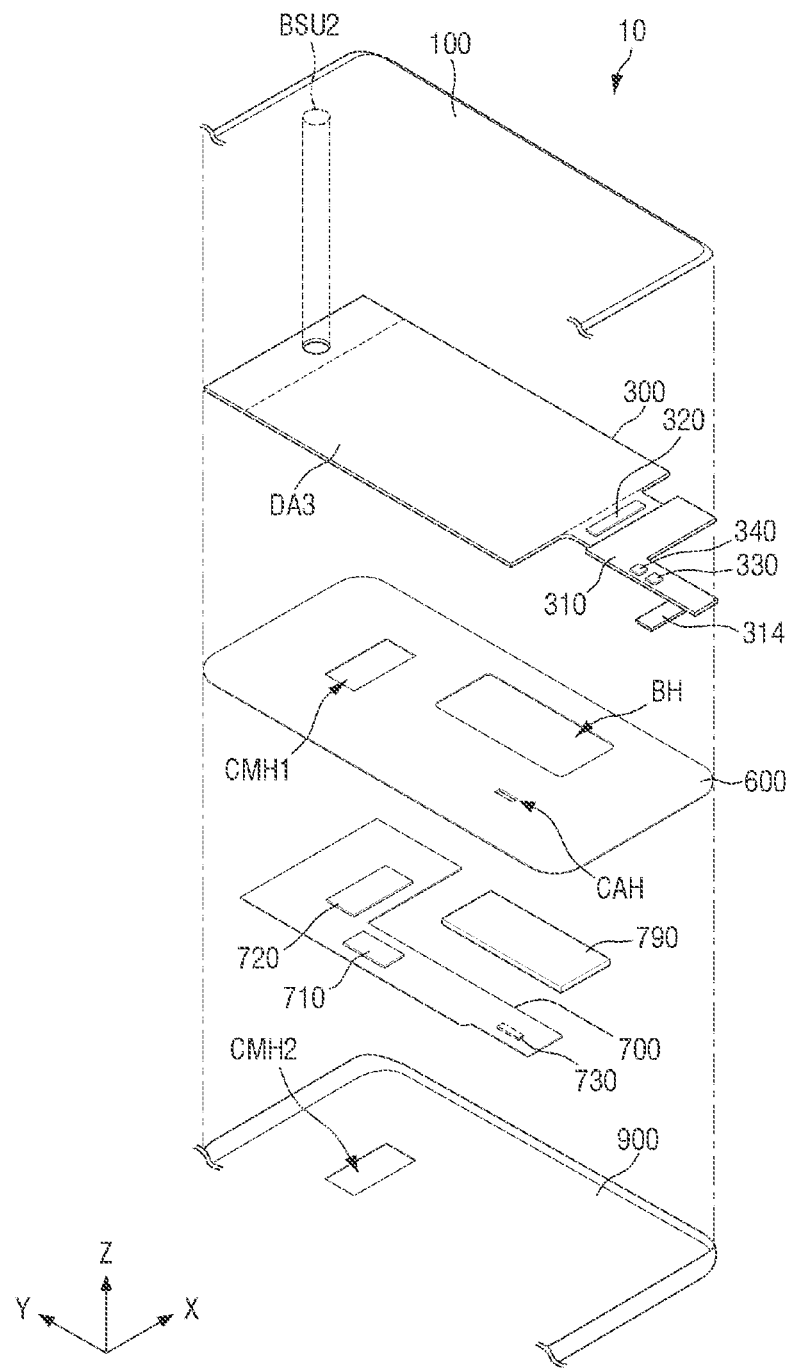
FIG. 4 is an exploded perspective view showing a portion of a display device according to one embodiment.

FIG. 4 is an exploded perspective view showing a portion of a display device 10 that corresponds to the third non-folding area DA3 according to one embodiment.

In the display device 10, the first and second non-folding areas DA1 and DA2, and the first and second folding areas FOU1 and FOU2 may include structures that are identical to, analogous to, and/or different from the structures illustrated in FIG. 4.

Referring to FIG. 4, the display device 10 includes a cover window 100, a display panel 300, a display circuit board 310, a display driving circuit 320, a bracket 600, a main circuit board 700, and a lower/back cover 900 (also illustrated in FIG. 2).

The cover window 100 may be disposed above (or in front of) the display panel 300 to cover the front surface of the display panel 300. The cover window 100 may protect the front surface of the display panel 300.

The display panel 300 may be disposed below/behind the cover window 100. Pixels for displaying an image may be formed in the image display area of the display panel 300, and an image non-display area may be formed in the peripheral region of the image display area and may include no pixels. The image non-display area may surround the image display area. The image display area may occupy most of the area of the display panel 300.

The display panel 300 may include the second pulse wave signal detection region/unit BSU2. The second pulse wave signal detection region BSU2 may be surrounded by the image display area. The second pulse wave signal detection region BSU2 may be surrounded by the image non-display area or may be disposed in an area between the image display area and the image non-display area. FIGS. 1 and 4 illustrate that the second pulse wave signal detection region BSU2 is disposed in the upper center of the display panel 300, but the position of the second pulse wave signal detection region BSU2 may depend on embodiments.

The second pulse wave signal detection region BSU2 of the display panel 300 may include a light receiving sensor for sensing light incident on the front surface of the second pulse wave signal detection region BSU2, a force sensor for detecting a force applied to the second pulse wave signal detection region BSU2, and/or a temperature sensor for sensing the temperature of the second pulse wave signal detection region BSU2. The light receiving sensor may include a light receiving element such as a photodiode or a phototransistor. The light receiving sensor may be a complementary metal oxide semiconductor (CMOS) image sensor or a charge coupled device (CCD) sensor capable of sensing light. The light receiving sensor may output an electrical signal and/or an optical signal to the main processor 710 according to the amount of light passing through or reflected from an object or a user body part disposed on the second pulse wave signal detection region BSU2. The main processor 710 may calculate or generate a pulse wave signal reflecting a change in blood flow according to heartbeats, according to the electrical signal and/or the optical signal. The main processor 710 may determine the user's blood pressure by analyzing at least one of a signal value at a specific time point, an amplitude (or a magnitude), a pulse width, a period, and a wave change of the pulse wave signal. A method of measuring a user's blood pressure based on the pulse wave signal is described with reference to FIGS. 5 to 7.

The display panel 300 may be a light emitting display panel including a light emitting element. The display panel 300 may be an organic light emitting display panel using an organic light emitting diode including an organic light emitting layer, a micro light emitting diode display panel using a micro LED, a quantum dot light emitting display panel using a quantum dot light emitting diode including a quantum dot light emitting layer, or an inorganic light emitting display panel using an inorganic light emitting element including an inorganic semiconductor. For example, the display panel 300 may be an organic light emitting display panel.

The display panel 300 may include a touch electrode layer having touch electrodes for sensing an object such as a human finger or a pen. The touch electrode layer may be disposed on a display layer in which pixels displaying an image are arranged.

The display circuit board 310 and the display driving circuit 320 may be attached to one side of the display panel 300. The display circuit board 310 may be a flexible printed circuit board which is bendable, a rigid printed circuit board which is hardly bendable, or a composite printed circuit board having both of a rigid printed circuit board and a flexible printed circuit board.

The display driving circuit 320 may receive control signals and power voltages through the display circuit board 310 to generate and output signals and voltages for driving the display panel 300. The display driving circuit 320 may be an integrated circuit (IC) attached on the display panel 300 by a chip-on-glass (COG) method, a chip-on-plastic (COP) method, or an ultrasonic bonding method. The display driving circuit 320 may be attached onto the display circuit board 310.

A touch driving circuit 330 and a force driving circuit 340 may be disposed on the display circuit board 310. Each of the touch driving circuit 330 and the force driving circuit 340 may be an IC attached to the top/front surface of the display circuit board 310. The touch driving circuit 330 and the force driving circuit 340 may be integrally formed as one IC.

The touch driving circuit 330 may be electrically connected to the touch electrodes of the touch electrode layer of the display panel 300 through the display circuit board 310. The touch driving circuit 330 may output a touch driving signal to the touch electrodes and sense the voltage charged in the capacitances of the touch electrodes.

The touch driving circuit 330 may generate touch data according to the change in the electrical signal sensed at the touch electrodes to transmit the touch data to a main processor 710. The main processor 710 may analyze the touch data to generate touch coordinates. The touch may include a contact touch and/or a proximity touch. The contact touch indicates that the object such as the human finger or pen makes a direct contact with the cover window disposed above the touch electrode layer. The proximity touch indicates that the object such as the human finger or pen is positioned and/or hovers above (or in front of) the cover window without directly contacting the cover window.

A power supply unit may be disposed on the display circuit board 310 to supply display driving voltages for driving the display driving circuit 320.

The bracket 600 may be disposed under the display panel 300. The bracket 600 may include plastic, metal, or both plastic and metal. A first camera hole CMH1 into which a first camera sensor 720 is inserted, a battery hole BH in which a battery is disposed, a cable hole CAH through which a cable 314 connected to the display circuit board 310 passes, and the like may be formed in the bracket 600. The main circuit board 700 and a battery 790 may be disposed under the bracket 600. The main circuit board 700 may be a printed circuit board or a flexible printed circuit board.

The main circuit board 700 may include a main processor 710, a first camera sensor 720, and a main connector 730. The first camera sensor 720 may be disposed on both the top and bottom surfaces of the main circuit board 700, the main processor 710 may be disposed on the top surface of the main circuit board 700, and the main connector 730 may be disposed on the bottom surface of the main circuit board 700.

The main processor 710 may control all functions of the display device 10. The main processor 710 may output digital video data to the display driving circuit 320 through the display circuit hoard 310 such that the display panel 300 displays an image. The main processor 710 may receive touch data from the touch driving circuit 330 and determine the user's touch coordinates, and then execute an application indicated by an icon displayed on the user's touch coordinates. The main processor 710 may convert first image data inputted from the first camera sensor 720 into digital video/image data and output it to the display driving circuit 320 through the display circuit board 310, thereby displaying an image captured by the first camera sensor 720 on the display panel 300. The main processor 710 may calculate a pulse wave signal reflecting the change in blood flow according to heartbeats, according to the optical signal inputted from the light receiving sensor and the like of the second pulse wave signal detection region BSU2. The main processor 710 may determine a user's blood pressure using an analysis result of the pulse wave signal based on the pulse wave signal.

The first camera sensor 720 may obtain and process an image frame of a still image or video and may output it to the main processor 710. The first camera sensor 720 may be a complementary metal-oxide-semiconductor (CMOS) image sensor or a charge-coupled device (CCD) sensor. The first camera sensor 720 may be exposed to the bottom surface of the lower cover 900 by a second camera hole CMH2 to thereby capture an image of a background or an object disposed below the display device 10.

The cable 314 may pass through the cable hole CAH of the bracket 600 and may be connected to the main connector 730. Thus, the main circuit board 700 may be electrically connected to the display circuit board 310.

The force driving circuit 340 may sense an electrical signal from the force sensor of the second pulse wave signal detection region BSU2, may convert the sensed signal into force data, and may transmit it to the main processor 710. The main processor 710 may determine whether force has been applied to the force sensor or not, and may calculate the magnitude of the force applied to the force sensor based on the force data.

The battery 790 may be disposed so as not to overlap the main circuit board 700 in the third direction (Z-axis direction). The battery 790 may overlap (and may be disposed in) the battery hole BH of the bracket 600.

The main circuit board 700 may be equipped with a mobile communication module capable of transmitting and receiving radio signals with at least one of a base station, an external terminal, and a server in a mobile communication network. The radio signals may include various types of data according to transmission and reception of a voice signal, a video call signal, or a text/multimedia message.

The lower cover 900 may be disposed below the main circuit hoard 700 and the battery 790. The lower cover 900 may be fastened to the bracket 600. The lower cover 900 may form an external appearance of the bottom surface of the display device 10. The lower cover 900 may include plastic, metal, or both plastic and metal.

The second camera hole CMH2 may expose the bottom surface of the first camera sensor 720 and may be formed in the lower cover 900. The position of the first camera sensor 720 and the positions of the first and second camera holes CMH1 and CMH2 corresponding to the first camera sensor 720 may depend on embodiments.

Figure 5:
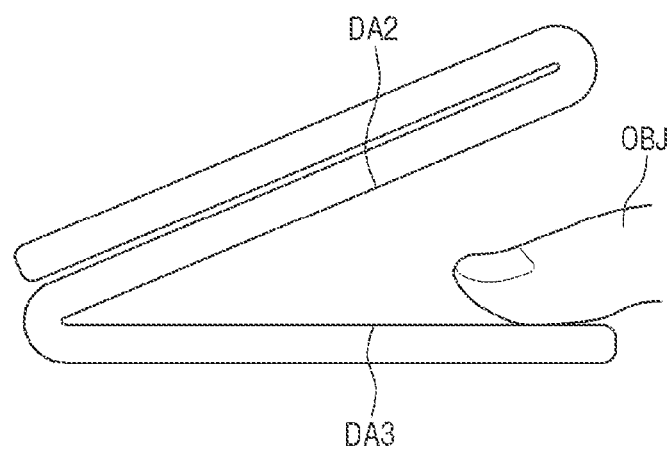
FIG. 5 is a schematic side view showing a display device measuring a blood pressure according to one embodiment.
Figure 6:
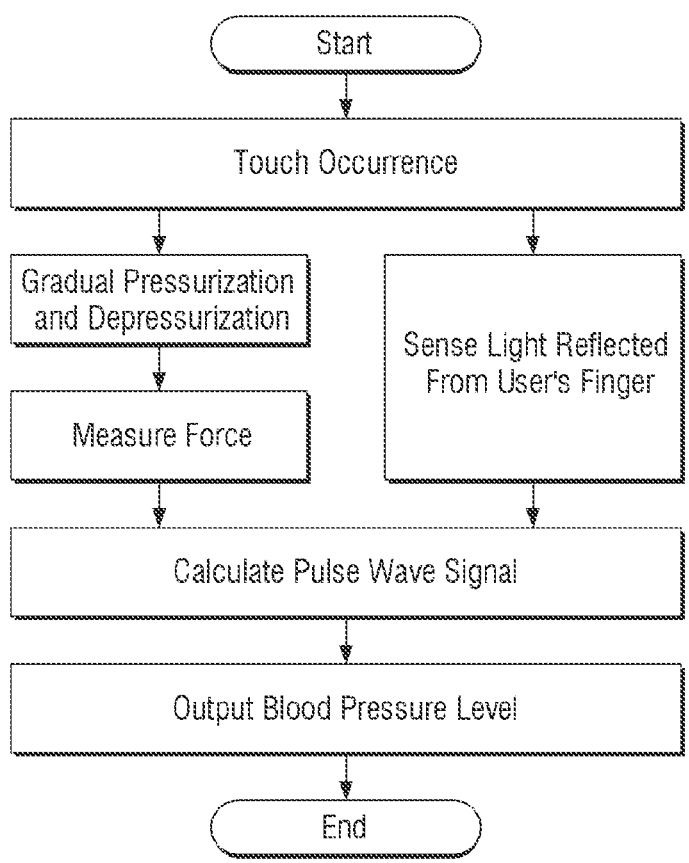
FIG. 6 is a flowchart illustrating a method of measuring a blood pressure performed by a display device according to one embodiment.

FIG. 5 is a schematic side view showing the display device measuring a blood pressure according to one embodiment. FIG. 6 is a flowchart illustrating a method of measuring a blood pressure by the display device according to one embodiment.

In the second pulse wave signal detection region BSU2 of the display panel 300, light incident from the front surface of the display device 10 may be sensed. In the first pulse wave signal detection region BSU1 of the second non-folding area DA2, light may be emitted toward the front side, or the light emitting member may emit light. At least one light receiving sensor included in the second pulse wave signal detection region BSU2 senses light that has passed through and/or reflected from a user body part such as a finger OBJ. For example, when the finger OBJ touches the front surface of the display device 10 in the second pulse wave signal detection region BSU2, the display device 10 may recognize that a touch has occurred. The display device 10 may recognize the user's touch through the force sensor or the touch electrode layer of the display panel 300.

When the display device 10 determines that a touch has occurred, the main processor 710 may operate in a blood pressure measurement mode. For example, when the user sets the blood pressure measurement mode through a program or application of the display device 10 before measuring a blood pressure, the display device 10 may perform blood pressure measurement according to the touch occurrence. The display device 10 may automatically switch to the blood pressure measurement mode after a touch occurs without the user's additional action for mode determination. When the user touches a position which is out of the blood pressure measurement position, the display device 10 may operate in a touch mode. When the user touches a position which corresponds to the blood pressure measurement position, the display device 10 may operate in the blood pressure measurement mode. When the user increases a touch force, the display device 10 may operate in the blood pressure measurement mode by force analysis of the force sensor.

The display device 10 may determine a blood pressure using both the light receiving sensor and the force sensor disposed in the second pulse wave signal detection region BSU2 in the blood pressure measurement mode. The main processor 710 may generate the pulse wave signal according to the force applied by the user, based on a force value calculated by the force sensor and/or the optical signal according to the amount of light sensed by the light receiving sensor. The main processor 710 may calculate the blood pressure based on the pulse wave signal. The pulse wave signal may have a waveform vibrating according to the cardiac cycle. The main processor 710 may estimate blood pressure values of the blood vessels of the finger OBJ based on a time difference between a time point corresponding to the maximum value of the calculated pulse wave signal and a time point corresponding to any one of the maximum, minimum, and average values of the filtered pulse wave. Among the estimated blood pressure values, a maximum blood pressure value may be determined as a systolic blood pressure value, and a minimum blood pressure value may be determined as a diastolic blood pressure value. Additional blood pressure values such as an average blood pressure value or the like may be calculated using the estimated blood pressure values. The calculated blood pressure may be displayed to the user through a display screen of at least one non-folding area of the display device 10.

Although FIGS. 5 and 6 illustrate the user's finger OBJ as the user's body part where the blood pressure is measured, the user's body part where the blood pressure is measured may be a wrist or another body part.

Figure 7:
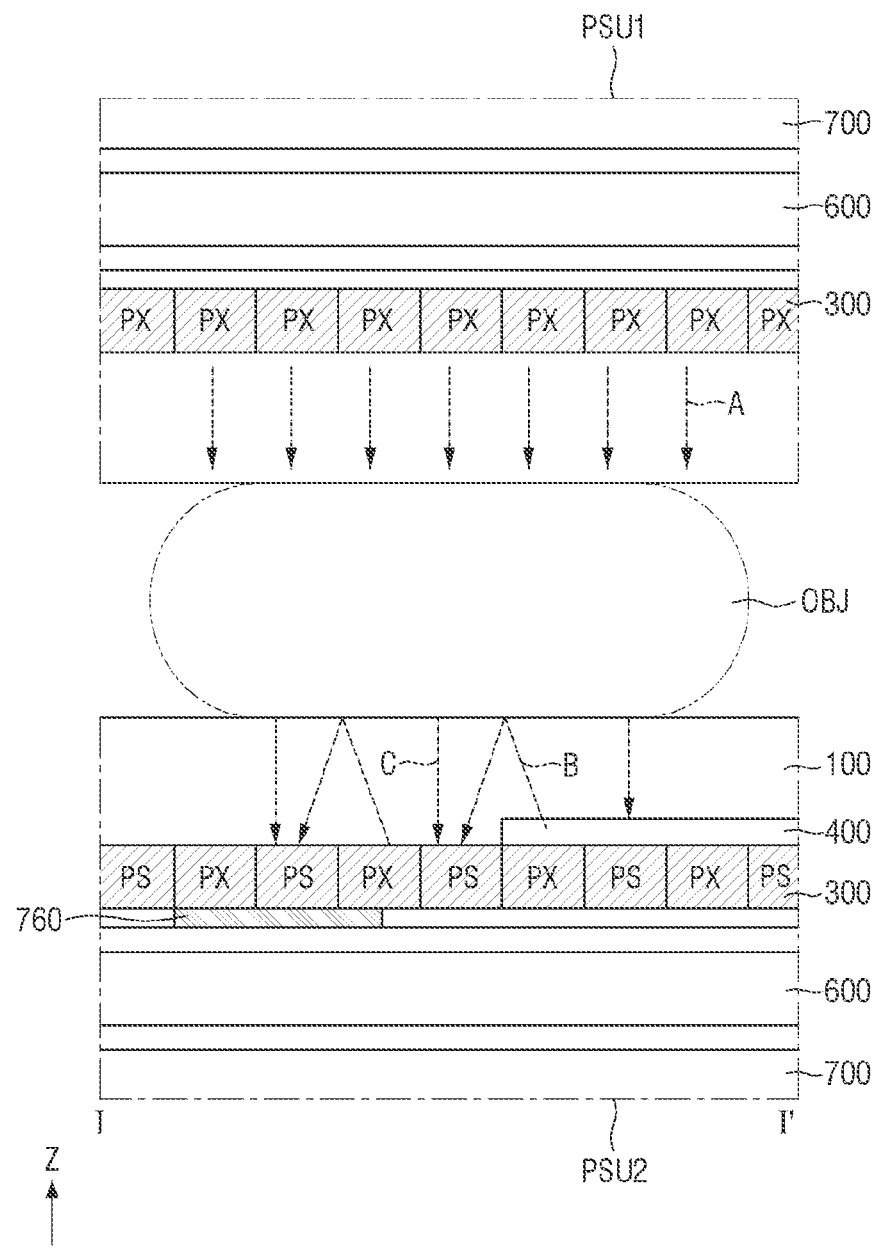
FIG. 7 is a cross-sectional view illustrating structures of a cover window, a display panel, a force sensor, a light receiving sensor, and the like included in pulse wave signal detection regions associated with line I-I' shown in FIG. 3 according to one embodiment.

FIG. 7 is a cross-sectional view illustrating structures of a cover window, a display panel, a force sensor, a light receiving sensor, and the like included in the first and second pulse wave signal detection regions/units BSU1 and BSU2 associated with line I-I' shown in FIG. 3 according to one embodiment. FIG. 7 omits the lower cover 900 for convenience of illustration.

Referring to FIG. 7, FIG. 1, FIG. 3, FIG. 4, and FIG. 5, the first pulse wave signal detection region/unit BSU1 (or first measurement enabling unit BSU1) may be formed/positioned in the second non-folding area DA2 of the display panel 300. The first pulse wave signal detection region BSU1 may include a plurality of image display pixels PX. The first pulse wave signal detection region BSU1 may include a plurality of light sensing pixels PS having a light receiving sensor. One or more of the light sensing pixels PS may be disposed between two immediately neighboring image display pixels PX. Each of the image display pixels PX disposed in the first pulse wave signal detection region BSU1 may emit light (light indicated by arrow A) having a predetermined brightness for detecting a pulse wave signal under the control of the main processor 710 during a touch sensing period. At least one light emitting member may be included in the first pulse wave signal detection region BSU1. The at least one light emitting member may emit light (light indicated by arrow A) having a predetermined brightness under the control of the main processor 710 during the touch sensing period. The at least one light emitting member may be disposed in a (through) hole of the display panel 300.

The second pulse wave signal detection region/unit BSU2 (or second measurement enabling unit BSU2) may be positioned in the third non-folding area DA3 of the display panel 300. The second pulse wave signal detection region BSU2 may include a force sensor 400 for detecting a force applied to the second pulse wave signal detection region BSU2, a temperature sensor 760 for sensing the temperature of the second pulse wave signal detection region BSU2, a plurality of image display pixels PX, and a plurality of light sensing pixels PS including light receiving sensors.

The force sensor 400 generates a sensing signal corresponding to a force applied to the second pulse wave signal detection region BSU2 under the control of the force driving circuit 340, and transmits it to the force driving circuit 340. The force sensor 400 may be disposed on one surface of the display panel 300. The force sensor 400 may be formed on a touch sensing layer of the display panel 300 or disposed on the rear surface of the display panel 300. The top surface of the force sensor 400 may be attached to the bottom surface of the display panel 300 by a transparent adhesive member.

The temperature sensor 760 may be disposed on one surface of the display panel 300. The temperature sensor 760 may be disposed on the front surface or the rear surface of the display panel 300. One surface of the temperature sensor 760 may be attached to the bottom surface of the display panel 300 by a transparent adhesive member.

The temperature sensor 760 may overlap an image display surface of the display panel 300 in the third direction (Z-axis direction). A portion of the temperature sensors 760 may overlap the image display surface of the display panel 300 in the third direction (Z-axis direction), and the other portion of the temperature sensors 760 may overlap the image non-display surface of the display panel 300 in the third direction (Z-axis direction).

At least one light sensing pixel PS may be disposed between two immediately neighboring image display pixels PX. Each of the light sensing pixels PS includes at least one light receiving sensor. The light receiving sensor may include a light receiving element such as a photodiode or a phototransistor. The light receiving sensors included in the light sensing pixels PS sense light that has passed through or has been reflected from a user body part, such as the finger OBJ.

As shown in FIG. 7, the lights (lights indicated by arrows A) emitted from the image display pixels PX of the first pulse wave signal detection region BSU1 may be partially absorbed by and/or partially pass through the blood vessels of the user's finger OBJ located between the pulse wave signal detection regions BSU1 and BSU2. The light (light indicated by arrow C) that has passed through the user's finger OBJ may be sensed by (the light receiving sensors of) the light sensing pixels PS of the second pulse wave signal detection region BSU2.

The main processor 710 of the display device 10 may detect and correct a pulse wave signal using one or more of the image display pixels PX, the force sensor 400, the temperature sensor 760, and the light receiving sensors to determine a blood pressure using the detected pulse wave signal in the blood pressure measurement mode.

As shown in FIG. 7, among the lights outputted from the image display pixels PX of the second detection region BSU2, light (light indicated by arrow B) reflected from the user's finger OBJ may be sensed by the light receiving sensors of the light sensing pixels PS. When a heart contracts, blood ejected from a left ventricle of the heart moves to peripheral tissues, which increases the arterial blood volume. Further, when the heart contracts, red blood cells carry more oxygen hemoglobin to the peripheral tissues. When the heart relaxes, the heart receives a partial influx of blood from the peripheral tissues. When light is irradiated to peripheral blood vessels, the irradiated light is absorbed by the peripheral tissues. Light absorbance depends on hematocrit and blood volume. The light absorbance may have a maximum value when the heart contracts and may have a minimum value when the heart relaxes. Therefore, light sensed by the light receiving sensor 740 may be the least when the heart contracts and may be the most when the heart relaxes.

When the user puts a finger on the display device 10 and lifts it off in the blood pressure measurement mode, a force (contact force) applied to the force sensor 400 may gradually increase to reach a maximum value, and then may gradually decrease. When the contact force increases, blood vessels may be narrowed, resulting in no blood flow. When the contact force decreases, the blood vessels expand, and thus blood flows again. A further decrease of the contact force results in greater blood flow. Therefore, the change in the amount of light sensed by the light receiving sensor may be proportional to the change in blood flow.

The first pulse wave signal detection region/unit BSU1 may be disposed in the second non-folding area DA3; the second pulse wave signal detection region/unit BSU2 may be disposed in the second non-folding area DA2.

Figure 8:
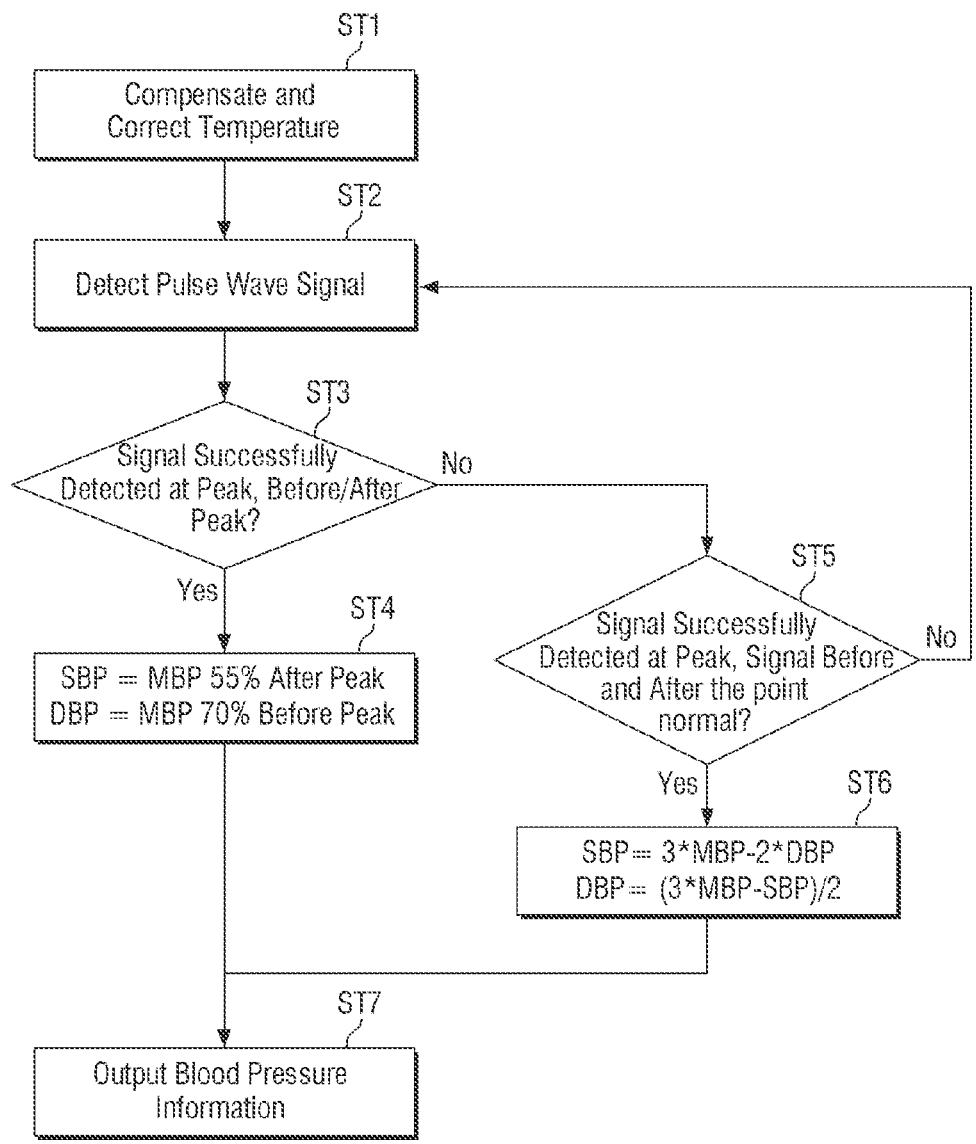
FIG. 8 is a flowchart illustrating a blood pressure measurement process performed by a main processor shown in FIG. 4 according to one embodiment.
Figure 9:
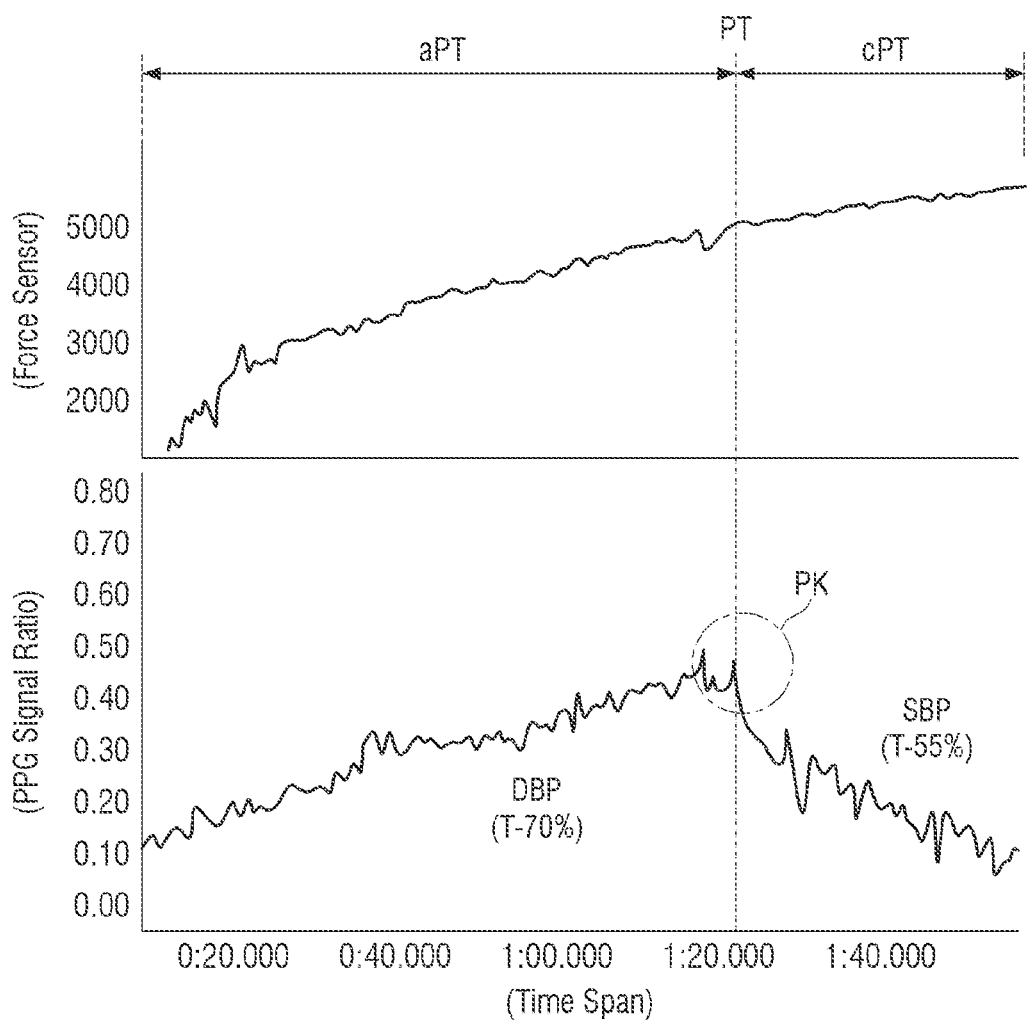
FIG. 9 is a graph for explaining a method of calculating a blood pressure performed by a main processor according to one embodiment.

FIG. 8 is a flowchart illustrating a blood pressure measurement process by the main processor 710 shown in FIG. 4 according to one embodiment. FIG. 9 is a graph for explaining a method of calculating a blood pressure by the main processor 710 according to one embodiment.

Referring to FIG. 4, FIG. 5, FIG. 6, FIG. 7, FIG. 8, and FIG. 9, the force sensor 400 senses a force applied to the second pulse wave signal detection region BSU2 and transmits a sensing signal according to the force sensing result to the force driving circuit 340. At substantially the same time, the temperature sensor 760 transmits a temperature sensing signal sensed in the second pulse wave signal detection region BSU2 to the main processor 710. The main processor 710 corrects force data of the force driving circuit 340 according to the magnitude of the temperature sensing signal. The main processor 710 generates temperature data according to the temperature sensing signal inputted in real time, and compares the temperature data with a reference temperature value of the display panel 300. The force data may be corrected by increasing or decreasing the force data value by a value corresponding to the difference value obtained by the comparison (step ST1).

The main processor 710 may monitor a force applied in real time according to the corrected force data. The main processor 710 may determine whether a touch has been made according to the force data value. When a touch is sensed, the main processor 710 detects a pulse wave signal (PPG signal ratio) according to an amount of light sensed by the light receiving sensors and/or an electrical signal corresponding to the amount of light, and then determines a peak detection value PK of the pulse wave signal according to the electrical signal during a force data detection and correction period (step ST2).

If the peak detection value PK of the pulse wave signal and the associated time information PT are (clearly) calculated, the main processor 710 may determine that the pulse wave signal has been successfully detected. If the peak detection value PK of the pulse wave signal and the associated time information PT are not (clearly) calculated, the main processor 710 may determine that the pulse wave signal is in an unstable state (step ST3).

If the peak detection value PK of the pulse wave signal and the detection time information PT of the peak detection value PK are calculated, the main processor 710 calculates each of diastolic blood pressure (DBP) information, mean blood pressure (MBP) information, and systolic blood pressure (SBP) information by analyzing the pulse wave signal during the previous and subsequent periods aPT and cPT according to the detection time PT of the peak detection value PK (step ST4).

Since the light absorbance has a maximum value when the heart contracts and has a minimum value when the heart relaxes, light sensed by the light receiving sensor 740 may be least when the heart contracts and may be largest when the heart relaxes. The main processor 710 may set a blood pressure value as the DBP (when the heart relaxes) according to the pulse wave signal detection value at a time in a range of 60 percent to 80 percent of the previous period aPT before the detection time PT of the peak detection value PK. The main processor 710 may set a blood pressure value as the SBP (when the heart contracts) according to the pulse wave signal detection value at a time in a range of 40 percent to 60 percent of the subsequent period cPT after the detection time PT of the peak detection value PK.

The main processor 710 may set the blood pressure value according to the pulse wave signal detection value at T-70%, i.e., at 70 percent of the previous period aPT before the detection time PT of the peak detection value PK, as the DBP. The main processor 710 may set the blood pressure value according to the pulse wave signal detection value at T-55%, i.e., at 55 percent of the subsequent period cPT after the detection time PT of the peak detection value PK, as the SBP. The MBP may be set according to the minimum to maximum blood pressure values. The blood pressure values corresponding to the light amount, the electrical signal associated with the light amount, and/or the pulse wave signal detection value are preset in a built-in memory or storage, for the main processor 710 to determine the blood pressure values corresponding to the pulse wave signal detection value. The main processor 710 may display information on the SBP, the DBP, and the MBP on the preset application program screen on the display panel 300 (step ST7).

In Step ST4, the values of the SBP, the DBP, and the MBP may be set by various methods, in addition to the method described with reference to FIG. 9.

The main processor 710 may not detect or identify the peak detection value PK of the pulse wave signal in step ST2 of detecting the peak detection value PK of the pulse wave signal and the associated time information PT. For example, when a plurality of detection values of the pulse wave signal are detected to have similar specific peak magnitudes, no peak detection value PK may be set, and no associated time information PT associated with the peak detection value PK may be detected.

If the peak detection value PK of the pulse wave signal is not detected and set, the main processor 710 calculates the lowest pulse wave signal value during the detection period of the peak detection value PK of the pulse wave signal (step ST5). For example, if the peak detection value PK of the pulse wave signal is not set in step ST3, the main processor 710 may detect the lowest pulse wave signal during a preset previous period and a preset subsequent period based on a time point when multiple detection values having similar specific peak magnitudes are detected. The main processor 710 may calculate an average pulse wave signal value during the detection period of the peak detection value PK in addition to detecting the lowest pulse wave signal value among the pulse wave signal detection values detected during the detection period of the peak detection value PK.

If the average pulse wave signal value and the lowest pulse wave signal value are determined, the main processor 710 may set the MBP corresponding to the average pulse wave signal value and set the DBP corresponding to the lowest pulse wave signal value. The main processor 710 may set the SBP and reset the DBP using Equations 1 below (step ST6).

$$SBP = \alpha \times MBP - \beta \times DBP$$

$$DBP = (\alpha \times MBP - SBP)/\beta \qquad \text{[Equations 1]}$$

Here, $\alpha$ and $\beta$ are positive integers that are equal to or different from each other. The main processor 710 may display information on the SBP, the DBP, and the MBP (obtained from Equations 1) on the preset application program screen on the display panel 300 (step ST7).

Figure 10:
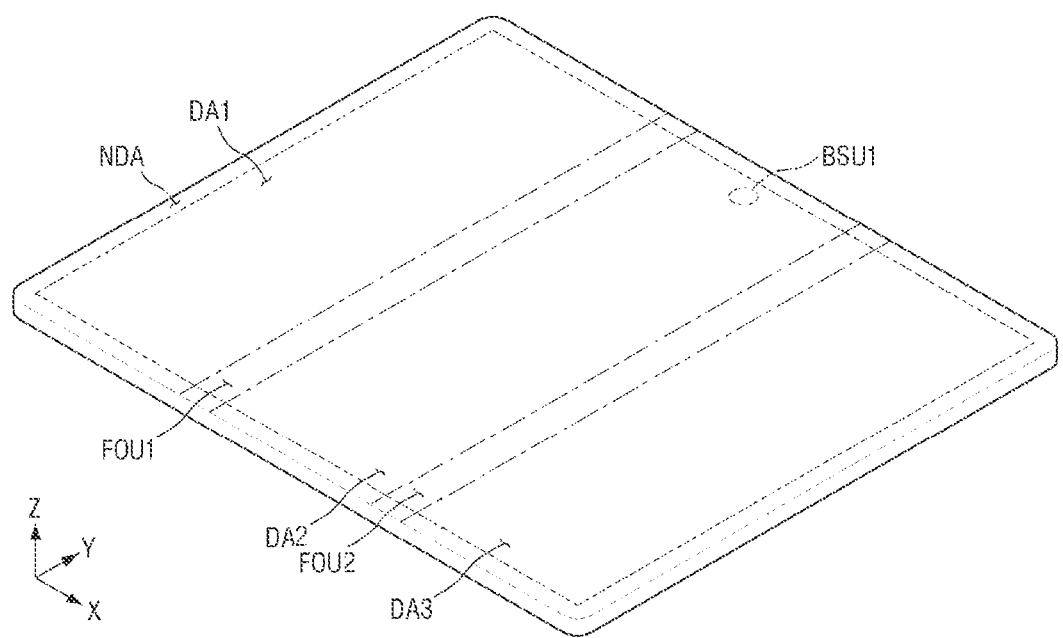
FIG. 10 is a schematic perspective view showing a display device according to one embodiment.
Figure 11:
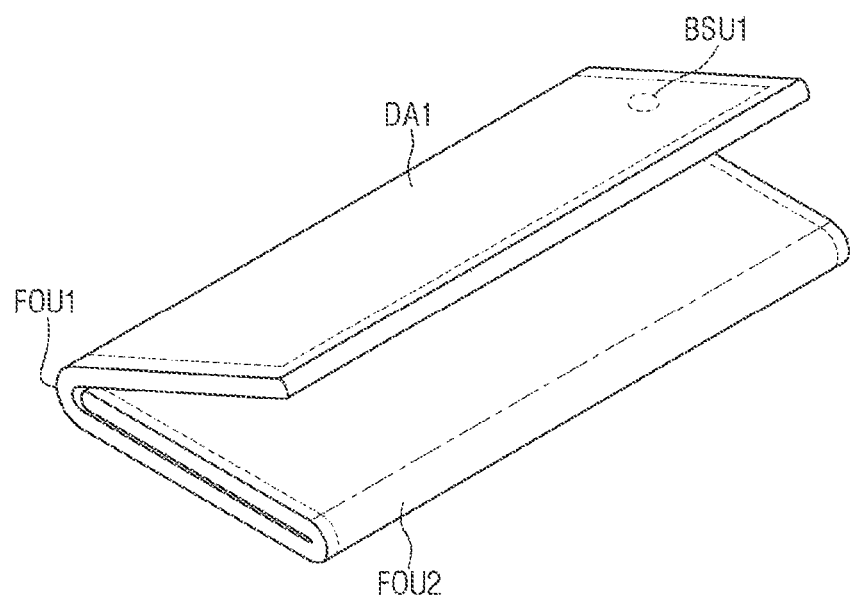
FIG. 11 is a perspective view illustrating a folding shape of a display device according to one embodiment.

FIG. 10 is a schematic perspective view showing a display device according to one embodiment. FIG. 11 is a perspective view illustrating a folding shape of a display device according to one embodiment.

As shown in FIGS. 10 and 11, a foldable image display area of a display device may include non-folding areas DA1, DA2, and DA3 and may include folding areas FOU1 and FOU2. The first and second folding areas FOU1 and FOU2 may be disposed at different locations in the first direction (X-axis direction) and may extend in the second direction (Y-axis direction).

The first folding area FOU1 may extend in the second direction (Y-axis direction) between the first and second non-folding areas DA1 and DA2. The first folding area FOU1 may be folded in the in-folding manner in the first direction (X-axis direction), so that the front/display surfaces of the first and second non-folding areas DA1 and DA2 may face each other. The second folding area FOU2 may extend in the second direction (Y-axis direction) between the second and third non-folding areas DA2 and DA3. The second folding area FOU2 may be folded in the in-folding manner in the first direction (X-axis direction), so that the front/display surfaces of the second and third non-folding areas DA2 and DA3 may also face each other.

The display device may form a G type or inverted G type foldable structure in which both the first and second folding areas FOU1 and FOU2 are folded in the in-folding manner so that the front surfaces of the second and third non-folding areas DA2 and DA3 face each other, and the front surface of the first non-folding area DA1 faces the rear surface of the third non-folding area DA3. When the display device 10 is folded in the G type or inverted G type structure, the length of the display device 10 in the first direction (X-axis direction) may be reduced to approximately ⅓ of its initial/unfolded value. Therefore, a user can conveniently carry the display device 10.

In the G type or inverted G type structure, a first pulse wave signal detection region BSU1 for detecting a pulse wave signal of a user body part (such as a finger) may be positioned in one of the first to third non-folding areas DA1 to DA3. For example, the first pulse wave signal detection region BSU1 may be positioned in the non-folding area DA1 or DA2.

Figure 12:
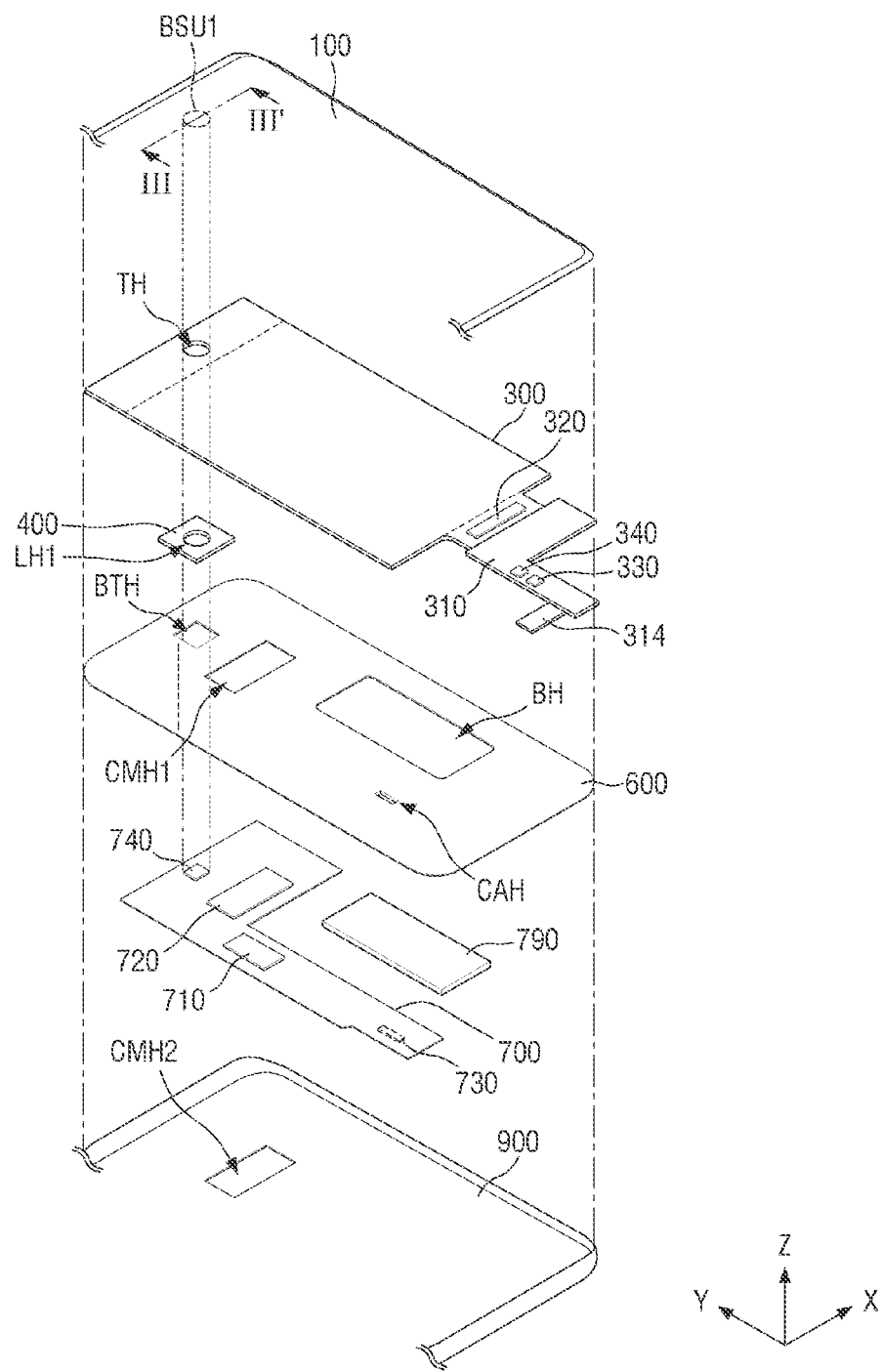
FIG. 12 is an exploded perspective view illustrating a portion of a display device according to one embodiment.

FIG. 12 is an exploded perspective view illustrating a non-folding area of the display device of FIG. 10 or FIG. 11 according to one embodiment.

One or more structures illustrated in FIG. 12 may be applicable to one or more of the non-folding areas DA1, DA2, and DA3 and/or one or both of the folding areas FOU1 and FOU2.

The display device includes a cover window 100, a display panel 300, a display circuit hoard 310, a display driving circuit 320, a bracket 600, a main circuit board 700, a light receiving sensor 740, and a lower cover 900.

The display panel 300 is disposed under the cover window 100. Pixels for displaying an image may be formed on the image display surface of the display panel 300, and a non-image display surface may be formed in the peripheral region of the image display surface without pixels. The image non-display surface may surround the image display surface. The image display surface may occupy most of the area of the display panel 300.

The display panel 300 may include a through hole TH formed in a region corresponding to the first pulse wave signal detection region BSU1. The through hole TH may penetrate the display panel 300. The through hole TH may be surrounded by the image display area.

The through hole TH may overlap a sensor hole BTH of the bracket 600 and the light receiving sensor 740 in the third direction (Z-axis direction). Therefore, light having passed through the through hole TH of the display panel 300 may be incident on the light receiving sensor 740 through the sensor hole BTH. Therefore, although the light receiving sensor 740 is disposed under the display panel 300, the light receiving sensor 740 may sense the light incident from the front surface of the display device 10.

The bracket 600 may be disposed under the display panel 300. The bracket 600 may include plastic, metal, or both plastic and metal. The bracket 600 may include a first camera hole CMH1 into which a first camera sensor 720 is inserted, a battery hole BH in which a battery is disposed, a cable hole CAH through which a cable 314 connected to the display circuit board 310 passes, and the sensor hole BTH overlapping the light receiving sensor 740 in the third direction (Z-axis direction). The light receiving sensor 740 may be arranged in the sensor hole BTH. The bracket 600 may not overlap a sub-display area of the display panel 300 and may not include a sensor hole.

The main circuit board 700 may include a main processor 710, a first camera sensor 720, a main connector 730, and the light receiving sensor 740. The first camera sensor 720 may be disposed on both the top and bottom surfaces of the main circuit board 700, the main processor 710 may be disposed on the top surface of the main circuit board 700, and the main connector 730 may be disposed on the bottom surface of the main circuit board 700. The light receiving sensor 740 may be disposed on the top surface of the main circuit board 700.

The main processor 710 may calculate a pulse wave signal reflecting a change in blood flow according to heartbeats, according to an electrical signal and/or an optical signal inputted from the light receiving sensor 740. A user's blood pressure may be determined using an analysis result of the pulse wave signal based on the pulse wave signal.

The light receiving sensor 740 may include a light receiving element capable of sensing light incident through the through hole TH. The light receiving element may be a photodiode or phototransistor. The light receiving sensor 740 may be a CMOS image sensor or a CCD sensor which is capable of sensing light. The light receiving sensor 740 may output an electrical signal and/or an optical signal to the main processor 710 according to the amount of light reflected from an object disposed above the through hole TH. The main processor 710 may calculate or generate a pulse wave signal reflecting a change in blood flow according to heartbeats, according to the electrical signal and/or the optical signal. The main processor 710 may determine the user's blood pressure by analyzing at least one of a signal value at a specific time point, an amplitude (or a magnitude), a pulse width, a period, and a wave change of the pulse wave signal.

The through hole TH may penetrate the display panel 300. The through hole TH may be an optical/transparent hole/part through which light may pass. The through hole TH may include a physical hole and an optical/transparent part.

Since the through hole TH overlaps the light receiving sensor 740 in the third direction (Z-axis direction), light having passed through the through hole TH may be incident on the light receiving sensor 740. The light receiving sensor 740 may sense the light incident from the front surface of the display device 10. The light receiving sensor 740 may sense light reflected from an object disposed above the through hole TH.

The through hole TH may be surrounded by the image display surface. The through hole TH may be surrounded by the image non-display surface or may be disposed between the image display surface and the image non-display surface.

Figure 13:
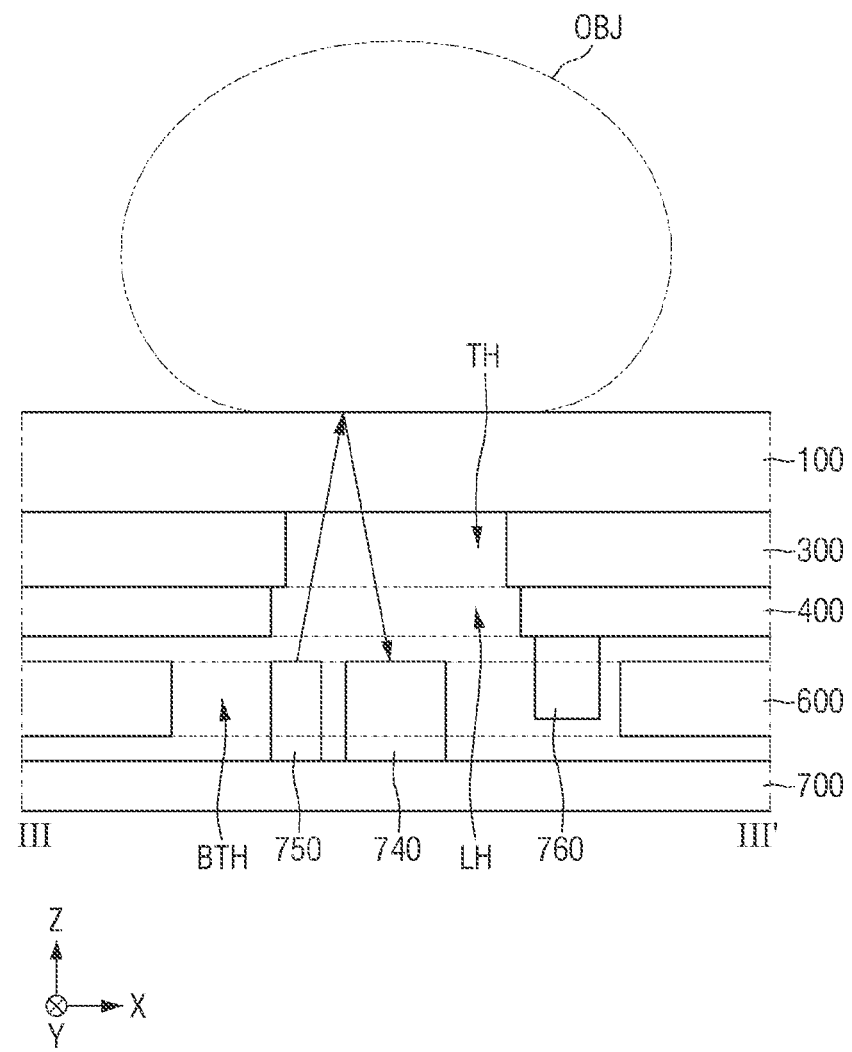
FIG. 13 is a cross-sectional view illustrating structures of a cover window, a display panel, a force sensor, a light emitting member, a light receiving sensor, and the like included in a pulse wave signal detection region associated with line III-III' shown in FIG. 12 according to one embodiment.

FIG. 13 is a cross-sectional view illustrating structures of a cover window, a display panel, a force sensor, a light emitting member, a light receiving sensor, and the like included in the first pulse wave signal detection region BSU1 associated with line Ill-III' shown in FIG. 12 according to one embodiment. The lower cover 900 is not illustrated in FIG. 13 for simplicity of description.

Referring to FIG. 13, the display device 10 may include a force sensor 400, a light emitting member 750, and a temperature sensor 760.

The force sensor 400 may be disposed on one surface of the display panel 300. The force sensor 400 may be disposed on the rear surface of the display panel 300. The front surface of the force sensor 400 may be attached to the rear surface of the display panel 300 by a transparent adhesive member.

The force sensor 400 may partially overlap the image display area of the display panel 300 in the third direction (Z-axis direction). A portion of the force sensor 400 may overlap the image display area of the display panel 300 in the third direction (Z-axis direction), and the remaining portion may overlap the image non-display area of the display panel 300 in the third direction (Z-axis direction). The force sensor 400 may include a first optical hole LH1. The first optical hole LH1 may be an optical/transparent hole/part through which light may pass. The first optical hole LH1 may be a physically formed hole (physical/empty hole) penetrating the force sensor 400. The first optical hole LH1 may include a physical hole and an optical/transparent part positioned inside the physical hole.

The through hole TH of the display panel 300 may be completely within the first optical hole LH1 of the force sensor 400 in a plan view of the display device. The size of the through hole TH of the display panel 300 may be smaller than the size of the first optical hole LH1 of the force sensor 400. The (maximum) length of the through hole TH in one direction may be smaller than the corresponding (maximum) length of the first optical hole LH1 in the one direction. For example, as illustrated in FIG. 13, the length of the through hole TH in the first direction (X-axis direction) may be smaller than the corresponding length of the first optical hole LH1 in the first direction (X-axis direction). Therefore, light having passed through the through hole TH may be incident on the underlying light receiving sensor 740 without being blocked by the force sensor 400.

The first optical hole LH1 of the force sensor 400 may be completely within the sensor hole BTH of the bracket 600 in a plan view of the display device. The size of the first optical hole LH1 of the force sensor 400 may be smaller than the size of the sensor hole BTH of the bracket 600. The (maximum) length of the first optical hole LH1 in one direction may be smaller than the corresponding (maximum) length of the sensor hole BTH in the one direction. For example, as illustrated in FIG. 13, the length of the first optical hole LH1 in the first direction (X-axis direction) may be smaller than the corresponding length of the sensor hole BTH in the first direction (X-axis direction). Therefore, light having passed through the through hole TH and the first optical hole LH1 may be incident on the underlying light receiving sensor 740 without being blocked by the bracket 600.

The light emitting member 750 may include a light source that emits light. The light source may have at least one of a light emitting diode (LED), an organic light emitting diode (OLED), a laser diode (LD), quantum dots (QD), and a phosphor.

The wavelength of light emitted from the light emitting member 750 may be an infrared wavelength, a visible wavelength, a wavelength of red light, or a wavelength of green light. When the user body part to be placed on the through hole TH is a finger OBJ (whose blood vessels are fine), the wavelength of the light emitted from the light emitting member 750 may be the infrared wavelength or the wavelength of red light. Since the infrared wavelength or the wavelength of red light is longer than the wavelength of green light or a wavelength of blue light, it is easy for the light to enter the blood vessels of the finger to be absorbed. When the user body part to be placed on the through hole TH is a wrist, the artery of the wrist is sufficiently thick. Therefore, even if the wavelength of the light emitted from the light emitting member 750 is the wavelength of green light, the green light may enter the artery of the wrist to be absorbed. The wavelength of the light emitted from the light emitting member 750 may be determined according to the body part subjected to blood pressure measurement.

The light receiving sensor 740 and the light emitting member 750 may be disposed on one surface of the main circuit board 700. The light receiving sensor 740 and the light emitting member 750 may be mounted side by side on the front surface of the main circuit board 700. The temperature sensor 760 may be disposed on the rear surface of the display panel 300 together with the force sensor 400, or may be disposed on the front surface of the display panel 300 or the rear surface of the force sensor 400.

The light receiving sensor 740 and the light emitting member 750 may overlap the through hole TH in the third direction (Z-axis direction). The light receiving sensor 740 and the light emitting member 750 may be arranged in the sensor hole of the bracket 600. When the lengths of the light receiving sensor 740 and the light emitting member 750 are relatively long in the third direction (Z-axis direction), the light receiving sensor 740 and the light emitting member 750 may be disposed in the first optical hole LH1 of the force sensor 400, or in both the through hole TH of the display panel 300 and the first optical hole LH1 of the force sensor 400. In this case, both the through hole TH of the display panel 300 and the first optical hole LH1 of the force sensor 400 may be the physical, empty holes.

As illustrated in FIG. 13, the light emitted from the light emitting member 750 may pass through the first optical hole LH1 of the force sensor 400 and the through hole TH of the display panel 300 to be absorbed by or reflected from the blood vessel of the user's finger OBJ. The light reflected from the blood vessel of the user's finger OBJ may pass through the through hole TH of the display panel 300 and the first optical hole LH1 of the force sensor 400 to be sensed by the light receiving sensor 740.

Figure 14:
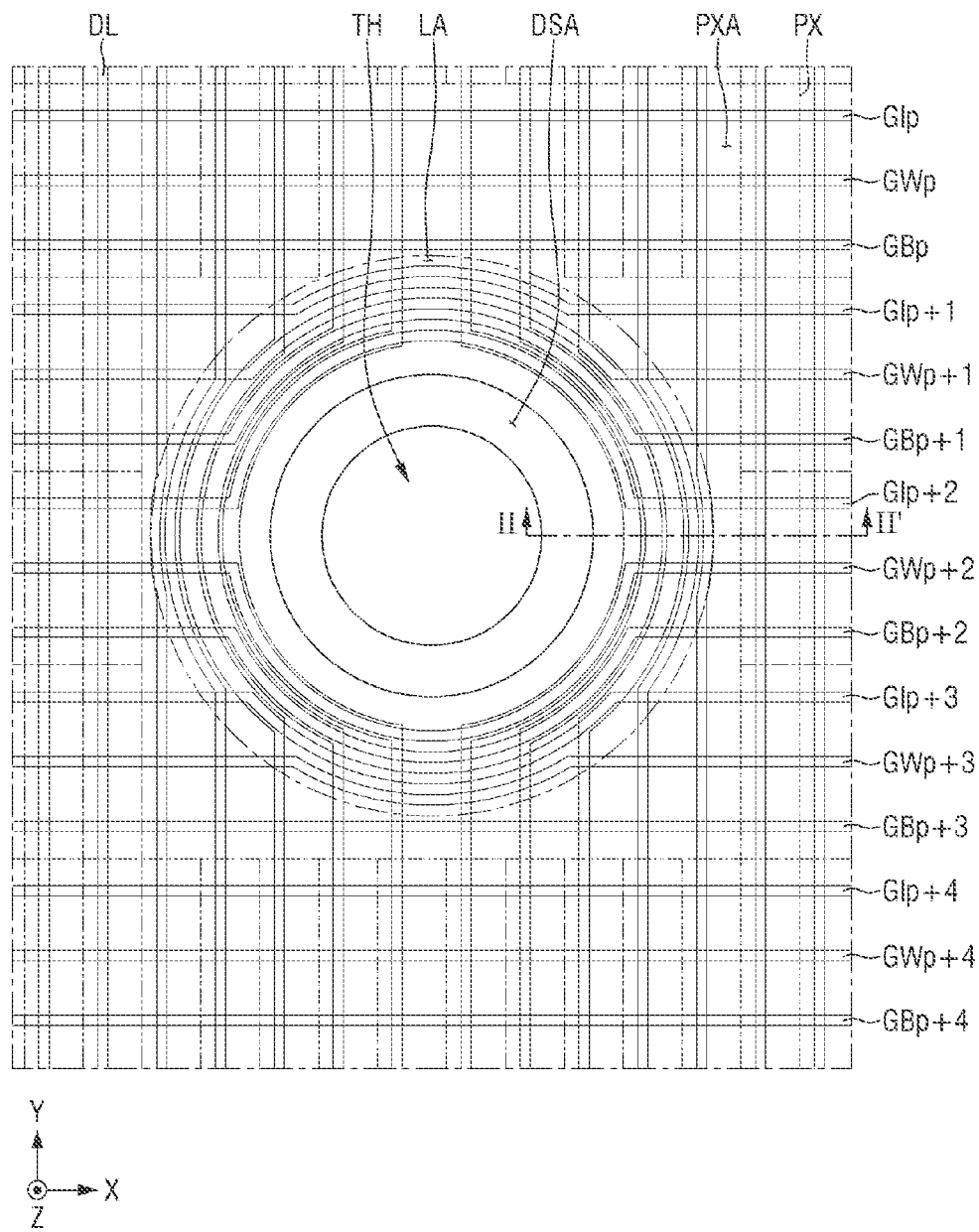
FIG. 14 is a layout diagram showing a display area and a through hole of a display panel according to one embodiment.

FIG. 14 is a layout diagram showing a display area and a through hole TH of a display panel according to one embodiment.

Referring to FIG. 14, the image display area may include the through hole TH, a dead space area DSA, a wiring area LA, and a pixel area PXA.

The dead space area DSA may surround the through hole TH. Pixels PX, scan lines SL, and data lines DL may not be disposed in the dead space area DSA. The dead space area DSA is for preventing the through hole TH from entering the wiring area LA due to a process error in the through hole TH forming process.

The wiring area LA may surround the dead space area DSA. Since no pixels PX are disposed in the wiring area LA, the wiring area LA is a non-display area that does not display an image.

The scan lines and the data lines DL that bypass the through hole TH may be disposed in the wiring area LA. The scan lines may include first initialization scan lines GIp, GIp+1, GIp+2, GIp+3, and GIp+4; write scan lines GWp, GWp+1, GWp+2, GWp+3, and GWp+4; and second initialization scan lines GBp, GBp+1, GBp+2, GBp+3, and GBp+4.

The first initialization scan lines GIp to GIp+4, the write scan lines GWp to GWp+4, and the second initialization scan lines GBp to GBp+4 may mostly extend in the first direction (X-axis direction). The first initialization scan lines GIp to GIp+4, the write scan lines GWp to GWp+4, and the second initialization scan lines GBp to GBp+4 may be curved in the second direction (Y-axis direction) to bypass the through hole TH. For example, among the first initialization scan lines GIp to GIp+4, the write scan lines GWp to GWp+4, and the second initialization scan lines GBp to GBp+4, scan lines that bypass the upper side of the through hole TH may be curved in the upper direction. Among the first initialization scan lines GIp to GIp+4, the write scan lines GWp to GWp+4, and the second initialization scan lines GBp to GBp+4, scan lines that bypass the lower side of the through hole TH may be curved in the lower direction. The first initialization scan lines GIp to GIp+4, the write scan lines GWp to GWp+4, and the second initialization scan lines GBp to GBp+4 may be bent in the form of a staircase to bypass the through hole TH.

The data lines DL may mostly extend in the second direction (Y-axis direction). The data lines DL may be curved in the first direction (X-axis direction) to bypass the through hole TH. For example, among the data lines DL, lines that bypass the left side of the through hole TH may be curved in the left direction. Among the data lines DL, lines that bypass the right side of the through hole TH may be curved in the right direction. The data lines DL may be bent in the form of a staircase to bypass the through hole TH.

In order to minimize the size of the wiring area LA, a distance between the scan lines adjacent to each other in the wiring area LA may be smaller than that in the pixel area PXA. Further, a distance between the data lines DL adjacent to each other in the wiring area LA may be smaller than that in the pixel area PXA. In the wiring area LA, scan lines may overlap data lines DL in the third direction (Z-axis direction).

Each of the pixels PX may be electrically connected to one of the first initialization scan lines GIp to GIp+4, one of the write scan lines GWp to GWp+4, and one of the second initialization scan lines GBp to GBp+4, and one of the data lines DL.

As illustrated in FIG. 14, the scan lines and the data lines DL may bypass the through hole TH in the wiring area LA, and the pixels PX are not arranged in the wiring area LA. Accordingly, even if the through hole TH is disposed to penetrate the image display area of the display panel 300, the display panel 300 may stably display an image.

Figure 15:
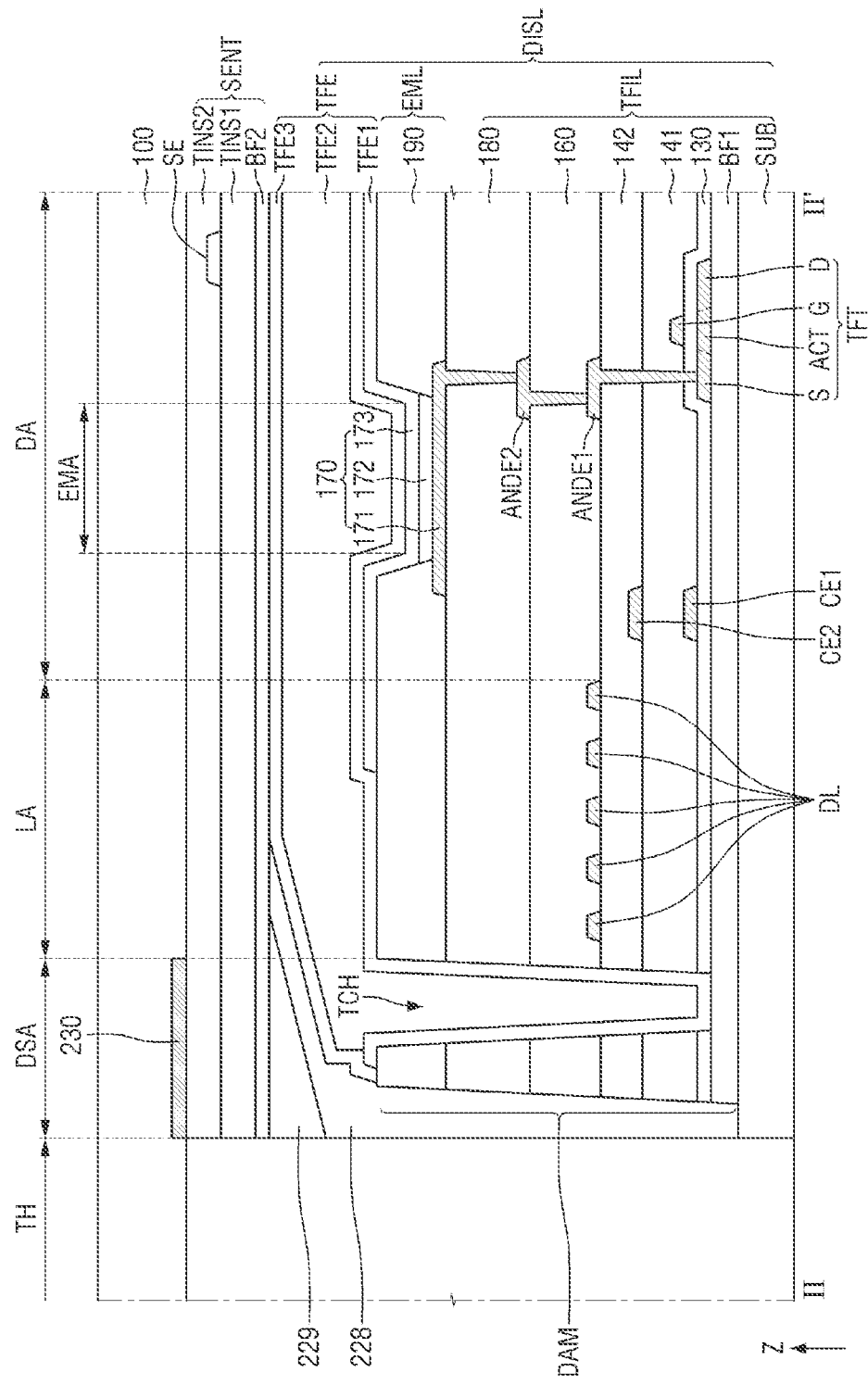
FIG. 15 is a cross-sectional view illustrating a structure of a display panel taken along line II-II' of FIG. 14 according to one embodiment.

FIG. 15 is a cross-sectional view illustrating a structure of a display panel taken along line II-II' of FIG. 14 according to one embodiment.

Referring to FIG. 15, a first buffer layer BF1, a thin film transistor layer TFIL, a light emitting element layer EML, an encapsulation layer TFE, and a touch electrode layer SENL may be sequentially disposed on the substrate SUB.

The substrate SUB may be formed of an insulating material such as glass, quartz, or a polymer resin. The substrate SUB may include polyimide. The substrate SUB may be a flexible substrate which can be bent, folded, and/or rolled.

The first buffer layer BF1 is a film for protecting thin film transistors TFT of the thin film transistor layer TFIL and a light emitting layer 172 of the light emitting element layer EML from moisture permeating through the substrate SUB. The first buffer layer BF1 may include inorganic layers that are alternately stacked. The first buffer layer BF1 may include inorganic layers of a silicon nitride layer, a silicon oxynitride layer, a silicon oxide layer, a titanium oxide layer and an aluminum oxide layer that are alternately stacked.

A light blocking layer may be disposed on the substrate SUB. The light blocking layer may overlap an active layer ACT of the thin film transistor TFT to prevent a leakage current occurring when light is incident on the active layer ACT of the thin film transistor TFT. The light blocking layer may be covered by the first buffer layer BF1. The light blocking layer may be/include a single layer or multiple layers made of at least one of molybdenum (Mo), aluminum (Al), chromium (Cr), gold (Au), titanium (Ti), nickel (Ni), neodymium (Nd), copper (Cu), and an alloy of some of the metal materials.

The thin film transistor layer TFIL includes the active layer ACT, a gate electrode G, a source electrode S, a drain electrode D, a gate insulating layer 130, a first interlayer insulating layer 141, a second interlayer insulating layer 142, a first planarization layer 160, and a second planarization layer 180.

The active layer ACT, the source electrode S, and the drain electrode D may be formed on the first buffer layer BF1. The active layer ACT may include polycrystalline silicon, monocrystalline silicon, low-temperature polycrystalline silicon, amorphous silicon, or an oxide semiconductor. When the active layer ACT is formed of polycrystalline silicon, the active layer ACT may have conductivity by ion doping. Therefore, the source electrode S and the drain electrode D may be formed by doping ions into active layers ACT.

The gate insulating layer 130 may be formed on the active layer ACT, the source electrode S, and the drain electrode D. The gate insulating layer 130 may be/include an inorganic layer, for example, a silicon nitride layer, a silicon oxynitride layer, a silicon oxide layer, a titanium oxide layer, or an aluminum oxide layer.

The gate electrode G and a first capacitor electrode CE1 may be formed on the gate insulating layer 130. The gate electrode G and the first capacitor electrode CE1 may be/include a single layer or multiple layers made of at least one of molybdenum (Mo), aluminum (Al), chromium (Cr), gold (Au), titanium (Ti), nickel (Ni), neodymium (Nd), copper (Cu), and an alloy of some of the metal materials.

The first interlayer insulating layer 141 may be formed on the gate electrode G and the first capacitor electrode CE1. The first interlayer insulating layer 141 may be/include an inorganic layer, for example, a silicon nitride layer, a silicon oxynitride layer, a silicon oxide layer, a titanium oxide layer, or an aluminum oxide layer. The first interlayer insulating layer 141 may include a plurality of inorganic layers.

A second capacitor electrode CE2 may be formed on the first interlayer insulating layer 141. The second capacitor electrode CE2 may be/include a single layer or multiple layers made of at least one of molybdenum (Mo), aluminum (Al), chromium (Cr), gold (Au), titanium (Ti), nickel (Ni), neodymium (Nd), copper (Cu), and an alloy of some of the metal materials.

The second interlayer insulating layer 142 may be formed on the second capacitor electrode CE2. The second interlayer insulating layer 142 may be/include an inorganic layer, for example, a silicon nitride layer, a silicon oxynitride layer, a silicon oxide layer, a titanium oxide layer, or an aluminum oxide layer. The second interlayer insulating layer 142 may include a plurality of inorganic layers.

A first anode connection electrode ANDE1 may be formed on the second interlayer insulating layer 142. The first anode connection electrode ANDE1 may be connected to the source electrode S through a contact hole penetrating the gate insulating layer 130, the first interlayer insulating layer 141, and the second interlayer insulating layer 142. The first anode connection electrode ANDE1 may be/include a single layer or multiple layers made of at least one of molybdenum (Mo), aluminum (Al), chromium (Cr), gold (Au), titanium (Ti), nickel (Ni), neodymium (Nd), copper (Cu), and an alloy of some of the metals.

The first planarization layer 160 may be formed on the first anode connection electrode ANDE1 to flatten steps formed due to the active layer ACT, the source electrode S, the drain electrode D, the gate electrode G, the first capacitor electrode CE1, the second capacitor electrode CE2 and the first anode connection electrode ANDE1. The first planarization layer 160 may be/include an organic layer formed of at least one of acryl resin, epoxy resin, phenolic resin, polyamide resin, and polyimide resin.

A protective layer may be additionally formed between the first anode connection electrode ANDE1 and the first planarization layer 160. The protective layer may be/include an inorganic layer, for example, a silicon nitride layer, a silicon oxynitride layer, a silicon oxide layer, a titanium oxide layer, or an aluminum oxide layer.

A second anode connection electrode ANDE2 may be formed on the first planarization layer 160. The second anode connection electrode ANDE2 may be connected to the first anode connection electrode ANDE1 through a contact hole penetrating the first planarization layer 160. The second anode connection electrode ANDE2 may be/include a single layer or multiple layers made of at least one of molybdenum (Mo), aluminum (Al), chromium (Cr), gold (Au), titanium (Ti), nickel (Ni), neodymium (Nd), copper (Cu), and an alloy of some of the metals.

The second planarization layer 180 may be formed on the second anode connection electrode ANDE2. The second planarization layer 180 may be/include an organic layer formed of at least one of acryl resin, epoxy resin, phenolic resin, polyamide resin, and polyimide resin.

Although FIG. 15 illustrates that the thin film transistor TFT is configured to be of a top gate type in which the gate electrode G is located on top of the active layer ACT, the thin film transistor TFT may be configured to be of a bottom gate type in which the gate electrode G is located under the active layer ACT, or a double gate type in which the gate electrode G is located on and under the active layer ACT.

The light emitting element layer EML is formed on the thin film transistor layer TFIL. The light emitting element layer EML includes light emitting elements 170 and a bank 190.

The light emitting elements 170 and the bank 190 are formed on the planarization layer 180. Each of the light emitting elements 170 may include a first light emitting electrode 171, the light emitting layer 172, and a second light emitting electrode 173.

The first light emitting electrode 171 may be formed on the second planarization layer 180. The first light emitting electrode 171 may be connected to the second anode connection electrode ANDE2 through a contact hole penetrating the second planarization layer 180.

In a top emission structure in which light is emitted toward the second light emitting electrode 173 from the light emitting layer 172, the first light emitting electrode 171 may be formed of a metal material having high reflectivity and may have a stacked structure (Ti—Al—Ti) of aluminum and titanium, a stacked structure (ITO-Al-ITO) of aluminum and ITO, an APC alloy, and a stacked structure (ITO-APC-ITO) of an APC alloy and ITO. The APC alloy is an alloy of silver (Ag), palladium (Pd), and copper (Cu).

The bank 190 may be formed on the second planarization layer 180 to partially expose the first light emitting electrode 171, thereby defining an emission area EMA. The bank 190 may cover the edge of the first light emitting electrode 171.

The bank 190 may be/include an organic layer formed of at least one of acryl resin, epoxy resin, phenolic resin, polyamide resin, and polyimide resin.

The emission area EMA represents an area in which the first light emitting electrode 171, the light emitting layer 172, and the second light emitting electrode 173 are sequentially stacked, and holes from the first light emitting electrode 171 and electrons from the second light emitting electrode 173 are combined with each other in the light emitting layer 172 to emit light.

The light emitting layer 172 is formed on the first light emitting electrode 171 and the bank 190. The light emitting layer 172 may include an organic material to emit light in a predetermined color. The light emitting layer 172 may include a hole transporting layer, an organic material layer, and an electron transporting layer.

The second light emitting electrode 173 is formed on the light emitting layer 172. The second light emitting electrode 173 may cover the light emitting layer 172. The second light emitting electrode 173 may be a common layer shared by multiple pixels. A capping layer may be formed on the second light emitting electrode 173.

In the top emission type structure, the second light emitting electrode 173 may be formed of a transparent conductive material (TCO) such as ITO or IZO capable of transmitting light or may be formed of a semi-transmissive conductive material such as magnesium (Mg), silver (Ag), or an alloy of magnesium (Mg) and silver (Ag). When the second light emitting electrode 173 is formed of a semi-transmissive conductive material, the light emission efficiency can be increased due to a micro-cavity effect.

The encapsulation layer TFE may be formed on the light emitting element layer EML. The encapsulation layer TFE may include at least one inorganic layer to prevent oxygen or moisture from permeating into the light emitting element layer EML. The encapsulation layer TFE may include at least one organic layer to protect the light emitting element layer EML from foreign substances such as dust. The encapsulation layer TFE may include a first inorganic layer TFE1, an organic layer TFE2, and a second inorganic layer TFE3.

The first inorganic layer TFE1, the organic layer TFE2 and the second inorganic layer TFE3 may be sequentially disposed on the second light emitting electrode 173. The first inorganic layer TFE1 and the second inorganic layer TFE3 may include multiple inorganic layers of a silicon nitride layer, a silicon oxynitride layer, a silicon oxide layer, a titanium oxide layer and an aluminum oxide layer that are alternately stacked. The organic layer TFE2 may be a monomer layer.

The touch electrode layer SENL is disposed on the encapsulation layer TFE. The touch electrode layer SENL includes a second buffer layer BF2, touch electrodes SE, and a first touch insulating layer TINS1.

The second buffer layer BF2 may be disposed on the encapsulation layer TFE. The second buffer layer BF2 may include at least one inorganic layer. The second buffer layer BF2 may include multiple inorganic layers of a silicon nitride layer, a silicon oxynitride layer, a silicon oxide layer, a titanium oxide layer and an aluminum oxide layer that are alternately stacked. The second buffer layer BF2 may be optional.

The first touch insulating layer TINS1 may be disposed on the second buffer layer BF2. The first touch insulating layer TINS1 may be/include an inorganic layer, for example, a silicon nitride layer, a silicon oxynitride layer, a silicon oxide layer, a titanium oxide layer, or an aluminum oxide layer. The first touch insulating layer TINS1 may be/include an organic layer formed of at least one of acryl resin, epoxy resin, phenolic resin, polyamide resin, and polyimide resin.

The touch electrodes SE may be disposed on the first touch insulating layer TINS1. The touch electrodes SE do not overlap the emission area EMA. That is, the touch electrodes SE are not disposed in the emission area EMA. Each of the touch electrodes SE may be a single layer formed of molybdenum (Mo), titanium (Ti), copper (Cu), or aluminum (Al), or may have a stacked structure (Ti—Al—Ti) of aluminum and titanium, a stacked structure (ITO-Al-ITO) of aluminum and indium tin oxide (ITO), an Ag—Pd—Cu (APC) alloy, or a stacked structure (ITO-APC-ITO) of APC alloy and ITO.

A second touch insulating layer TINS2 may be disposed on the touch electrodes SE. The second touch insulating layer TINS2 may include at least one of an inorganic layer and an organic layer. The inorganic layer may be a silicon nitride layer, a silicon oxynitride layer, a silicon oxide layer, a titanium oxide layer, or an aluminum oxide layer. The organic layer may include acryl resin, epoxy resin, phenolic resin, polyamide resin, or polyimide resin.

The cover window 100 may be disposed on the touch electrode layer SENL. A polarizing layer and an impact absorbing layer may be additionally disposed between the touch electrode layer SENL and the cover window 100.

A dam structure DAM may be disposed around the through hole TH. The dam structure DAM may include portions of some of the insulating layers BF1, 130, 141, 142, 160, 180, and 190. A trench TCH formed from partially removing the insulating layers BF1, 130, 141, 142, 160, 180, and 190 may be disposed between the dam structure DAM and the emission area EMA. At least a portion of the encapsulation layer TFE may be partially disposed in the trench TCH. For example, the organic layer TFE2 of the encapsulation layer TFE may be partially disposed in the trench TCH up to the dam structure DAM, and may not be disposed between the dam structure DAM and the through hole TH. The DAM may prevent organic material of the organic layer TFE2 from overflowing into the through hole TH. FIG. 15 illustrates that the first inorganic layer TFE1 and the second inorganic layer TFE3 end on the dam structure DAM. The first inorganic layer TFE1 and the second inorganic layer TFE3 may end in an area between the dam structure DAM and the through hole TH.

A light blocking pattern 230 may be disposed on one surface of the cover window 100. The light blocking pattern 230 may overlap the dam structure DAM in the third direction (Z-axis direction). The light blocking pattern 230 may overlap the edge of the through hole TH in the third direction (Z-axis direction).

At least one organic layer 228 and/or 229 may be disposed on the encapsulation layer TFE in the area between the dam structure DAM and the through hole TH. The first organic layer 228 may be disposed on the second inorganic layer TFE3, and a second organic layer 229 may be disposed on the first organic layer 228. The first organic layer 228 and the second organic layer 229 may fill the space between the dam structure DAM and the through hole TH to perform planarization.

Figure 16:
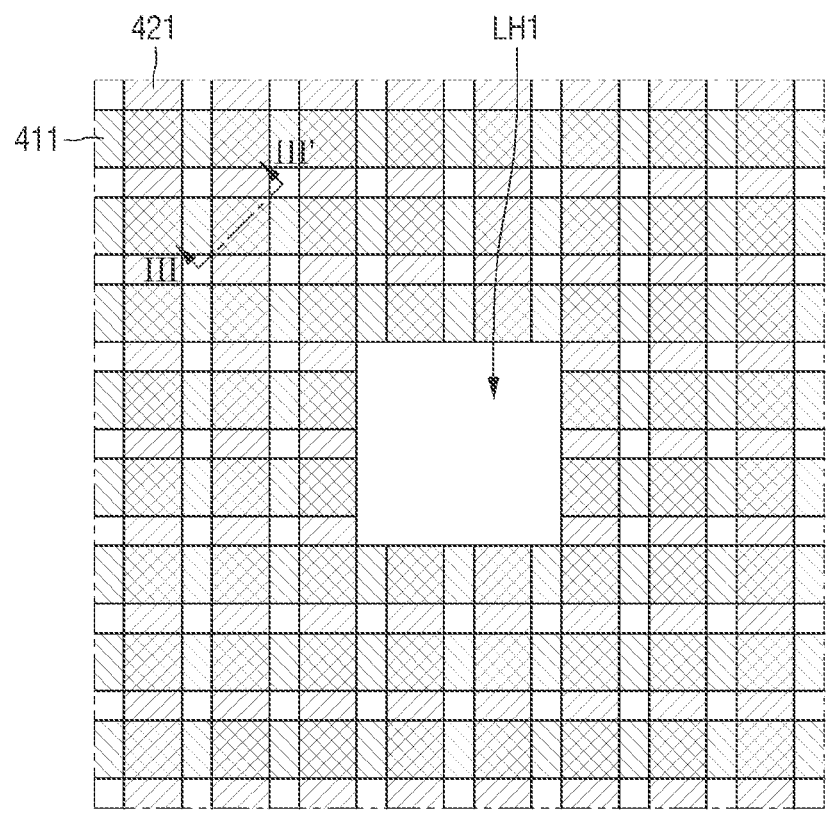
FIG. 16 is a layout view showing force sensor electrodes and a first optical hole of a force sensor according to one embodiment.
Figure 17:
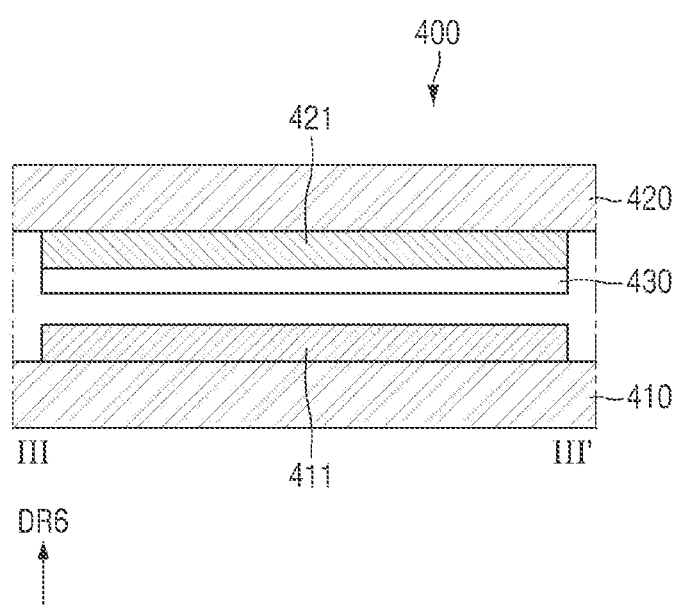
FIG. 17 is a cross-sectional view showing an example of the force sensor of FIG. 16 according to one embodiment.

FIG. 16 is a layout view showing force sensor electrodes and a first optical hole/part of a force sensor according to one embodiment. FIG. 17 is a cross-sectional view showing the force sensor of FIG. 16 corresponding to line III-III' according to one embodiment.

Referring to FIGS. 16 and 17, the force sensor 400 may include a first base substrate 410, a first force sensor electrode 411, a second base substrate 420, a second force sensor electrode 421, and a force sensing layer 430 disposed between the first force sensor electrode 411 and the second force sensor electrode 421 in the sixth direction DR6.

Each of the first base substrate 410 and the second base substrate 420 may include a polyethylene, polyimide, polycarbonate, polysulfone, polyacrylate, polystyrene, polyvinyl chloride, polyvinyl alcohol, polynorbornene, or polyester-based material. In one embodiment, each of the first base substrate 410 and the second base substrate 420 may be/include a polyethylene terephthalate (PET) film or a polyimide film.

The first base substrate 410 and the second base substrate 420 may be bonded to each other by a bonding layer. The bonding layer may include an adhesive material. The bonding layer may be disposed along the edges of the first base substrate 410 and the second base substrate 420.

The first force sensor electrodes 411 may be disposed on one surface of the first base substrate 410 that faces the second base substrate 420. The second force sensor electrodes 421 may be disposed on one surface of the second base substrate 420 that faces the first base substrate 410. Each of the first force sensor electrode 411 and the second force sensor electrode 421 may include a conductive material. For example, each of the first force sensor electrode 411 and the second force sensor electrode 421 may be made of a metal such as silver (Ag) or copper (Cu), a transparent conductive oxide such as ITO, IZO, or ZIO, carbon nanotubes, or conductive polymers. One of the first force sensor electrode 411 and the second force sensor electrode 421 may be a force driving electrode, and the other may be a force sensing electrode.

The force sensing layer 430 may be disposed between the first force sensor electrode 411 and the second force sensor electrode 421. The force sensing layer 430 may be in direct contact with at least one of the first force sensor electrode 411 and the second force sensor electrode 421. For example, the force sensing layer 430 may directly contact the second force sensor electrode 421.

The force sensing layer 430 may include a force sensitive material. The force sensitive material may contain metal nanoparticles formed of, for example, nickel, aluminum, tin, and/or, and/or may contain carbon. The force sensitive material may be particles provided in polymer resin.

When a force is applied to the force sensor 400, the first force sensor electrode 411, the force sensing layer 430, and the second force sensor electrode 421 may be electrically connected with each other. According to the force applied to the force sensor 400, electrical resistance of the force sensing layer 430 may become lower. The electrical resistance of the force sensing layer 430 may be calculated by applying a force driving voltage to the first force sensor electrode 411 and measuring a force sensing voltage through the second force sensor electrode 421. According to the electrical resistance of the force sensing layer 430, it is possible to determine whether a force has been applied or not and to calculate the magnitude of the force.

The first force sensor electrodes 411 may extend in a fourth direction DR4 and may be arranged in a fifth direction DR5. The second force sensor electrodes 421 may extend in the fifth direction DR5 and may be arranged in the fourth direction DR4. The first force sensor electrodes 411 and the second force sensor electrodes 421 may cross each other. Intersections of the first force sensor electrodes 411 and the second force sensor electrodes 421 may be arranged in a matrix/array. Each of the intersections of the first force sensor electrodes 411 and the second force sensor electrodes 421 may be a force sensing cell for sensing a force. A force may be sensed at one or more of the intersections of the first force sensor electrodes 411 and the second force sensor electrodes 421.

When the first force sensor electrode 411 and the second force sensor electrode 421 include an opaque conductive material or the force sensing layer 430 includes an opaque polymer resin, the force sensor 400 may be opaque. In order to prevent light, which has passed through the through hole TH, from being blocked by the force sensor 400, the force sensor 400 may include the first optical hole LH1. The opaque materials of the first force sensor electrodes 411, the second force sensor electrodes 421, and the force sensing layer 430 may be partially removed to form the first optical hole LH1. When the first force sensor electrodes 411 and the second force sensor electrodes 421 include an opaque conductive material, the first force sensor electrodes 411 and the second force sensor electrodes 421 may be partially removed from the first optical hole LH1. When the force sensing layer 430 includes an opaque polymer resin, the force sensing layer 430 may be removed from the first optical hole LH1. When the first force sensor electrode 411 and the second force sensor electrode 421 include an opaque conductive material, and the force sensing layer 430 includes an opaque polymer resin, the first force sensor electrodes 411, the second force sensor electrodes 421, and the force sensing layer 430 may be partially removed from the first optical hole LH1.

The first force sensor electrode 411, the second force sensor electrode 421, and the force sensing layer 430 may be included in the first base substrate 410 and the second base substrate 420. The first force sensor electrode 411 and the force sensing layer 430 may be included in the first base substrate 410, and the second force sensor electrode 421 may be included in the second base substrate 420. The first force sensor electrode 411, the second force sensor electrode 421, and the force sensing layer 430 may be included in one of the first base substrate 410 and the second base substrate 420.

FIG. 16 illustrates eight first force sensor electrodes 411 and eight second force sensor electrodes 421 for simplicity of description, but the numbers of the first force sensor electrodes 411 and the second force sensor electrodes 421 depend on embodiments. The lengths of the force sensor 400 in the fourth direction DR4 and in the fifth direction DR5 may be in a range of 10 mm to 20 mm. The lengths of the intersection of the first force sensor electrode 411 and the second force sensor electrode 421 in the fourth direction DR4 and the fifth direction DR5 may be about 1.5 mm or more. The lengths of the first optical hole LH1 in the fourth direction DR4 and in the fifth direction DR5 may be about 3 mm or more.

Figure 18:
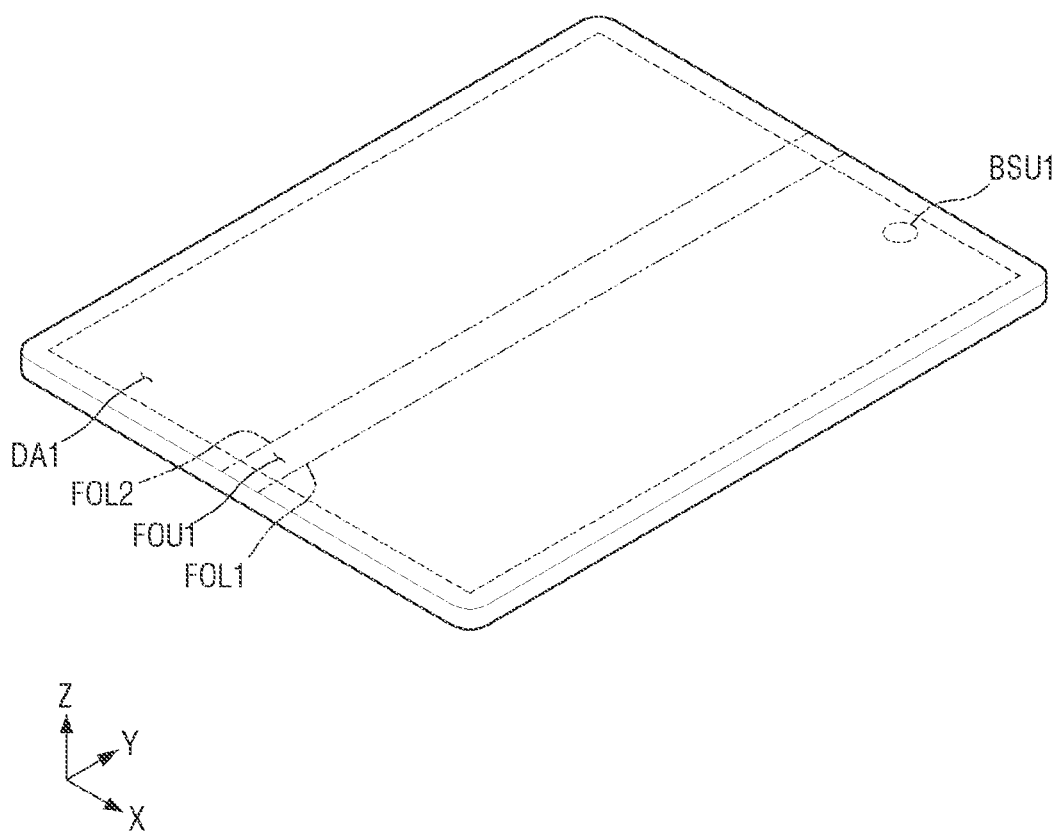
FIG. 18 and FIG. 19 are perspective views illustrating a display device according to one or more embodiments.
Figure 19:
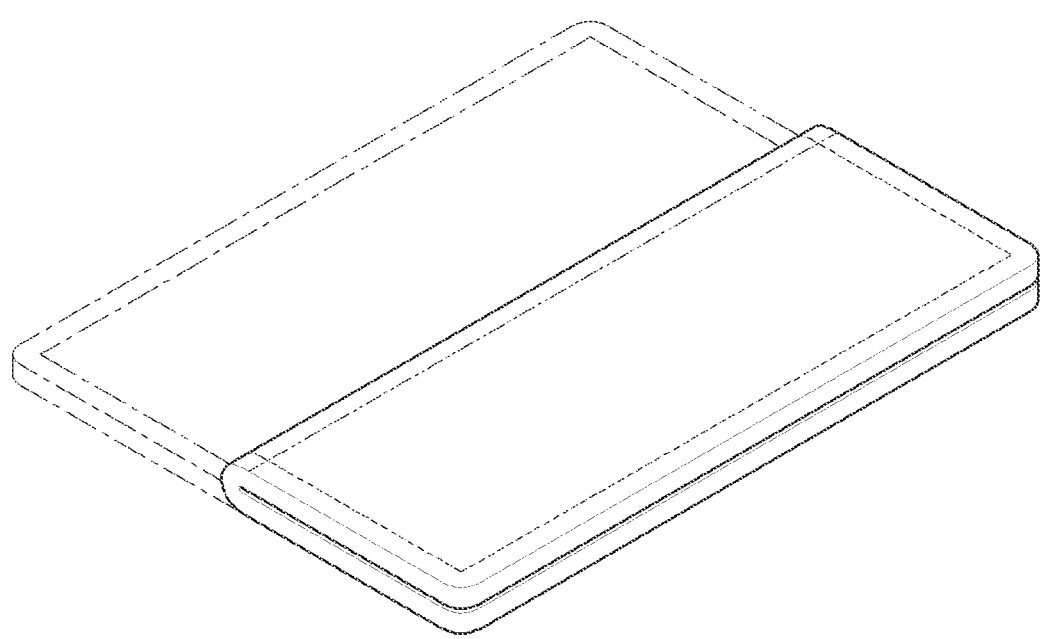
Figure 19:
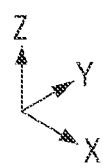

FIGS. 18 and 19 are perspective views illustrating a display device 10 according to one embodiment.

The display device 10 may be folded at first folding area FOU1 and may be folded in the first direction (X-axis direction). The display device 10 may maintain in a folded state or an unfolded state. The display device 10 may be folded in an in-folding manner in which the front display surfaces of the display device 10 may face each other. The display device 10 may be folded in an out-folding manner in which the rear surfaces of the display device 10 may face each other.

The first folding area FOU1 may be positioned between the first non-folding area DA1 and the second non-folding area DA2 in the first direction X when the display device 10 is unfolded.

The first folding area FOU1 and first and second folding lines FOL1 and FOL2 may extend in the second direction (Y-axis direction), and the display device 10 may be folded in the first direction (X-axis direction). Accordingly, the length of the display device 10 in the first direction (X-axis direction) may be reduced to approximately half, so that a user can conveniently carry the display device 10.

Folding lines may extend in the first direction (X-axis direction), and the display device 10 may be folded in the second direction (Y-axis direction). The length of the display device 10 in the second direction (Y-axis direction) may be reduced to approximately half. Folding lines may extend in a diagonal direction between the first direction (X-axis direction) and the second direction (Y-axis direction). The display device 10 may be folded in a triangular shape.

When the first folding line FOL1 and the second folding line FOL2 extend in the second direction (Y-axis direction), the length of the first folding area FOU1 in the first direction (X-axis direction) may be smaller than the length of the first folding area FOU1 in the second direction (Y-axis direction). The length of the first non-folding area DA1 in the first direction (X-axis direction) may be greater than the length of the first folding area FOU1 in the first direction (X-axis direction). The length of the second non-folding area DA2 in the first direction (X-axis direction) may be greater than the length of the first folding area FOU1 in the first direction (X-axis direction).

A first image display area may be disposed on the front surface of the display device 10. The first image display area may overlap with the first folding area FOU1, and the first and second non-folding areas DA1 and DA2. Therefore, when the display device 10 is unfolded, an image may be displayed in the first folding area FOU1, the first non-folding area DA1, and the second non-folding area DA2 of the display device 10.

A second image display area may be disposed on the rear surface of the display device 10. The second image display area may overlap the non-folding area DA1 or DA2. Therefore, when the display device 10 is folded, an image may be displayed in the second image display area and may be visible to the user.

A first pulse wave signal detection region BSU1 for detecting a pulse wave signal may be formed in one non-folding area DA1 or DA2. FIGS. 18 and 19 illustrate that the first pulse wave signal detection region BSU1 is arranged in the second non-folding area DA2.

Figure 20:
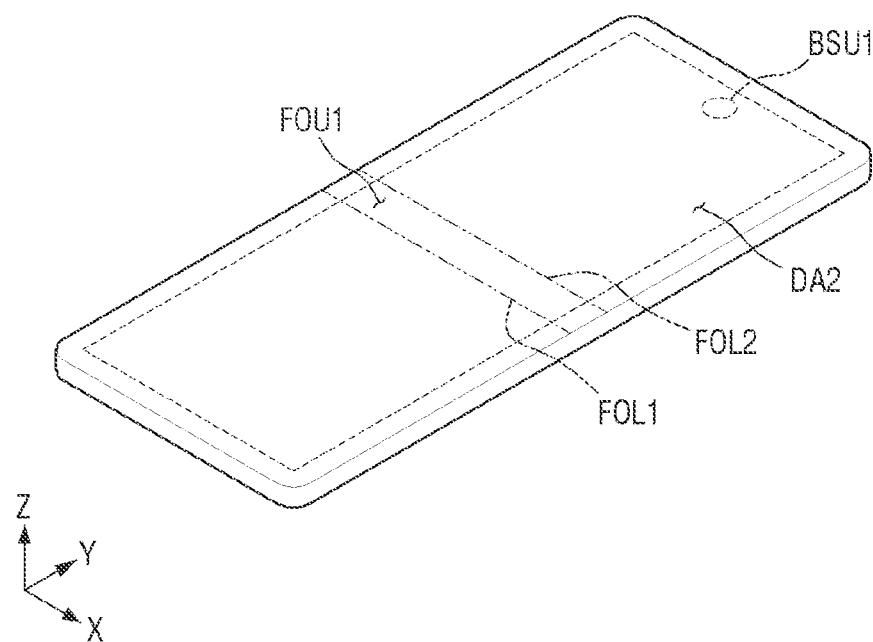
FIG. 20 and FIG. 21 are perspective views illustrating a display device according to one or more embodiments.
Figure 21:
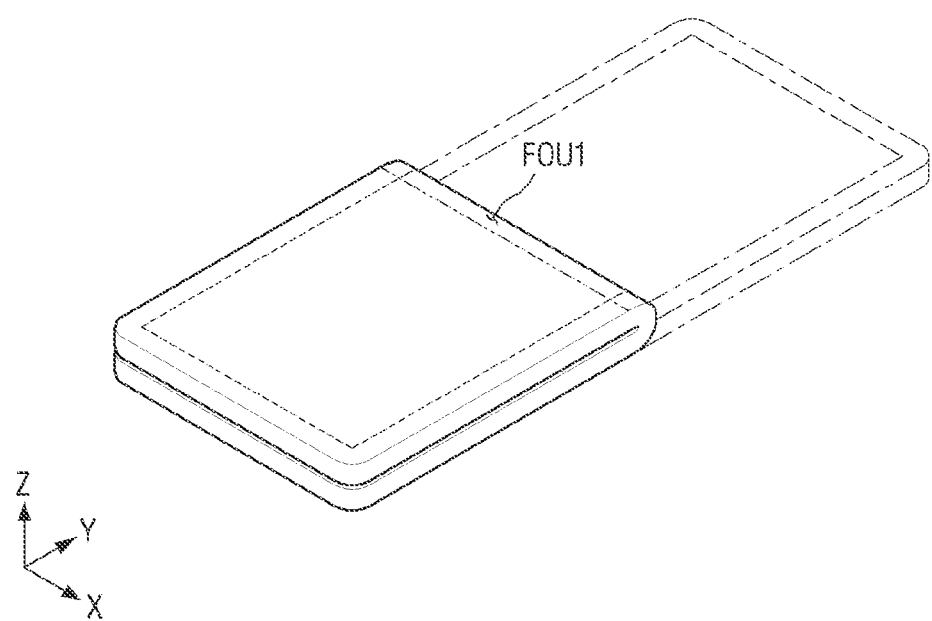

FIGS. 20 and 21 are perspective views illustrating a display device 10 according to still another embodiment.

The display device 10 may be folded at a first folding area FOU1 and may be folded in the second direction (Y-axis direction). The display device 10 may maintain in a folded state or an unfolded state. The display device 10 may be folded in an in-folding manner in which the front display surfaces of the display device 10 may face each other. The display device 10 may be folded in an out-folding manner in which the rear surfaces of the display device 10 may face each other.

The display device 10 may include the first folding area FOU1, a first non-folding area DA1, and a second non-folding area DA2. The display device 10 may be folded at the first folding area FOU1 and may not be folded at the first non-folding area DA1 or the second non-folding area DA2.

The first folding area FOU1 may be positioned between the first non-folding area DA1 and the second non-folding area DA2 in the second direction Y. The first folding area FOU1 may be bendable at a predetermined curvature at the first folding line FOL1 and the second folding line FOL2.

The first folding line FOL1 is a boundary between the first folding area FOU1 and the first non-folding area DA1, and the second folding line FOL2 is a boundary between the first folding area FOU1 and the second non-folding area DA2.

The first folding line FOL1 and the second folding line FOL2 may extend in the first direction (X-axis direction). The display device 10 may be folded in the second direction (Y-axis direction). The length of the display device 10 in the second direction (Y-axis direction) may be reduced to approximately half, so that a user can conveniently carry the display device 10.

A folding area may extend in the second direction (Y-axis direction), and the display device 10 may be folded in the first direction (X-axis direction). The length/width of the display device 10 in the first direction (X-axis direction) may be reduced to approximately half. A folding area FOU1 may extend in a diagonal direction between the first direction (X-axis direction) and the second direction (Y-axis direction). The display device 10 may be folded in one or more triangular shapes.

When the first folding area FOU1 extends in the first direction (X-axis direction), the length of the first folding area FOU1 in the second direction (Y-axis direction) may be smaller than the length thereof in the first direction (X-axis direction). The length of the first non-folding area DA1 in the second direction (Y-axis direction) may be greater than the length of the first folding area FOU1 in the second direction (Y-axis direction). The length of the second non-folding area DA2 in the second direction (Y-axis direction) may be greater than the length of the first folding area FOU1 in the second direction (Y-axis direction).

The first image display area may be disposed on the front surface of the display device 10. The first image display area may overlap with the first folding area FOU1, and the first and second non-folding areas DA1 and DA2. Therefore, when the display device 10 is unfolded, an image may be displayed in the first folding area FOU1, the first non-folding area DA1, and the second non-folding area DA2 of the display device 10.

A second image display area may be disposed on the rear surface of the display device 10. The second image display area may overlap with the non-folding area DA1 or DA2. When the display device 10 is folded, an image may be displayed in the second image display area and may be visible to the user.

A first pulse wave signal detection region BSU1 for detecting a pulse wave signal may be formed in one non-folding area DA1 or DA2. FIGS. 20 and 21 illustrate that the first pulse wave signal detection region BSU1 is disposed in the second non-folding area DA2.

In concluding the detailed description, the described embodiments are illustrative. Many variations and modifications can be made to the described embodiments without substantially departing from the scope of the claims.

What is claimed is:

1. A display device comprising:
   a display panel configured to display an image and comprising a first non-folding part, a second non-folding part, and a first folding part, wherein the first non-folding part is connected through the folding part to the second non-folding part;
   a first measurement enabling unit disposed in or overlapping with the first non-folding part and configured to emit first light;
   a second measurement enabling unit disposed in or overlapping with the second non-folding part and configured to output a first signal in response to at least one of a received force and received light; and
   a processor connected to the second measurement enabling unit and configured to use the first signal to determine a blood pressure value.

2. The display device of claim 1, wherein the display panel further comprises a second folding part and a third non-folding part, wherein the first folding part is positioned between the first non-folding part and the second non-folding part in a first direction when the display panel is unfolded, and wherein the second folding part is positioned between the first non-folding part and the third non-folding part in the first direction when the display panel is unfolded.

3. The display device of claim 2, wherein when the first folding part is folded in an in-folding manner, the first measurement enabling unit overlaps the second measurement enabling unit.

4. The display device of claim 2, wherein a width of the first folding part in the first direction is different from a width of the second folding part in the first direction when the display panel is completely unfolded.

5. The display device of claim 1, wherein the first measurement enabling unit comprises at least one of a first light emitting pixel set and a first light emitting member configured to emit the first light, and wherein the first non-folding part comprises at least one of a first hole and a first transparent part configured to transmit the first light.

6. The display device of claim 5, wherein the second measurement enabling unit comprises:
   a force sensor configured to detect the received force;
   a temperature sensor configured to sense a temperature of the display panel;
   a second light emitting pixel set; and
   a light sensor set, wherein at least one of the force sensor and the temperature sensor overlaps at least one of a light emitting pixel of the second light emitting pixel set and a light sensor of the light sensor set.

7. The display device of claim 6, wherein the processor generates a wave signal according to the first signal,
   identifies a peak value of the wave signal,
   identifies a peak value time corresponding to the peak value, and
   determines values of a diastolic blood pressure, a mean blood pressure, and a systolic blood pressure by analyzing values in the wave signal during a preceding period and a subsequent period, wherein the preceding period precedes the peak value time, and wherein the subsequent period follows the peak value time.

8. The display device of claim 6, wherein the force sensor comprises at least one of an opening and a transparent member that overlap with both the second light emitting pixel set and the light sensor set.

9. The display device of claim 6, wherein light sensors of the light sensor set and light emitting pixels of the second light emitting pixel set are alternately disposed, and wherein the light sensor set generates the first signal according to an amount of the received light.

10. The display device of claim 6, wherein the processor generates temperature data according to a temperature sensing signal inputted from the temperature sensor, compares the temperature data with a preset temperature reference value to generate a difference value, and corrects a force data size of the force sensor to a size corresponding to the difference value.

11. The display device of claim 7, wherein the processor sets a blood pressure value according to a wave signal value at a time in a range of 60 percent to 80 percent of the preceding period as a value of the diastolic blood pressure,
- wherein the processor sets a blood pressure value according to a wave signal value at a time in a range of 40 percent to 60 percent of the subsequent period as a value of the systolic blood pressure, and
- wherein the processor calculates the mean blood pressure using the diastolic blood pressure and the systolic blood pressure.

12. The display device of claim 7, wherein the processor sets a blood pressure value according to a wave signal value of 70 percent of the preceding period as the value of the diastolic blood pressure, and
- wherein the processor sets a blood pressure value according to a wave signal value of 55 percent of the subsequent period as the value of the systolic blood pressure.

13. The display device of claim 7, wherein if the peak value of the wave signal is not determined during a detection period of the peak value, the processor calculates an average wave signal value and a lowest wave signal value,
- sets a value of the mean blood pressure according to an average wave signal value, and sets or resets values of the systolic blood pressure and the diastolic blood pressure using Equations 1:

$$SBP = \alpha \times MBP - \beta \times DBP$$

$$DBP = (\alpha \times MBP - SBP)/\beta \qquad \text{[Equations 1]}$$

Wherein the $\alpha$ and the $\beta$ are positive integers that are equal to or different from each other, and
- wherein the SBP is a value of the systolic blood pressure, the DBP is a value of the diastolic blood pressure, and the MBP is the value of the mean blood pressure.

14. The display device of claim 6, wherein the first measurement enabling unit overlaps the second measurement enabling unit when an image display surface of the first non-folding part faces an image display surface of the second non-folding part.

15. A display device comprising:
- a display panel configured to display an image and comprising a first non-folding part, a second non-folding part, and a first folding part, wherein the first non-folding part is connected through the folding part to the second non-folding part;
- a measurement enabling unit disposed in or overlapping with the first non-folding part and configured to output a first signal in response to at least one of a received force and received light; and
- a processor connected to the measurement enabling unit and configured to use the first signal to determine a blood pressure value.

16. The display device of claim 15, wherein the measurement enabling unit comprises:
- a force sensor formed configured to detect the received force;
- a temperature sensor configured to sense a temperature of the display panel;
- at least one light emitting element spaced from at least one of the force sensor and the temperature sensor; and
- at least one light sensor spaced from one or both of the force sensor and the temperature sensor.

17. The display device of claim 15, wherein the measurement enabling unit comprises:
- a force sensor configured to sense the received force and comprising at least one of an opening and a transparent part;
- a light sensor overlapped with the at least one of the opening and the transparent part and configured to sense the received light; and
- a temperature sensor spaced from the light sensor and configured to sense a temperature of the display panel.

18. The display device of claim 17, wherein the processor generates temperature data according to a temperature sensing signal inputted from the temperature sensor, compares the temperature data with a preset temperature reference value to generate a difference value, and corrects a force data size of the force sensor according to the difference value.

19. The display device of claim 17, wherein the display panel comprises at least one of a hole and a transparent member, wherein the measurement enabling unit overlaps with at the at least one of the hole and the transparent member in a thickness direction of the display panel, wherein the measurement enabling unit further comprises a light emitting member configured to emit emitted light, and wherein the received light is a reflected portion of the emitted light.

20. The display device of claim 19, wherein the processor generates a wave signal according to the first signal,
- identifies a peak value of the wave signal,
- identifies a peak value time corresponding to the peak value, and
- determines values of a diastolic blood pressure, a mean blood pressure, and a systolic blood pressure by analyzing values in the wave signal during a preceding period and a subsequent period, wherein the preceding period precedes the peak value time, and wherein the subsequent period follows the peak value time.

* * * * *